(12) United States Patent
Song et al.

(10) Patent No.: US 9,790,276 B2
(45) Date of Patent: *Oct. 17, 2017

(54) GLYCAN-MODIFIED ANTI-CD4 ANTIBODIES FOR HIV PREVENTION AND THERAPY

(71) Applicant: THE ROCKEFELLER UNIVERSITY, New York, NY (US)

(72) Inventors: Ruijiang Song, Rego Park, NY (US); David D. Ho, Chappaqua, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 14 days.

This patent is subject to a terminal disclaimer.

(21) Appl. No.: 14/132,667

(22) Filed: Dec. 18, 2013

(65) Prior Publication Data

US 2015/0166662 A1 Jun. 18, 2015
US 2016/0362493 A9 Dec. 15, 2016

Related U.S. Application Data

(60) Provisional application No. 61/738,777, filed on Dec. 18, 2012, provisional application No. 61/864,942, filed on Aug. 12, 2013.

(51) Int. Cl.
*A61K 39/00* (2006.01)
*A61K 39/42* (2006.01)
*C07K 16/28* (2006.01)

(52) U.S. Cl.
CPC .... *C07K 16/2812* (2013.01); *A61K 2039/505* (2013.01); *C07K 2317/24* (2013.01); *C07K 2317/33* (2013.01); *C07K 2317/41* (2013.01); *C07K 2317/76* (2013.01)

(58) Field of Classification Search
None
See application file for complete search history.

(56) References Cited

U.S. PATENT DOCUMENTS

| 8,637,024 | B2 | 1/2014 | Ho et al. |
| 2006/0269543 | A1 | 11/2006 | Chu |
| 2009/0252724 | A1 | 10/2009 | Loetscher et al. |
| 2012/0121597 | A1 | 5/2012 | Ho et al. |
| 2014/0248295 | A1 | 9/2014 | Song et al. |

(Continued)

FOREIGN PATENT DOCUMENTS

| EP | 2377886 A1 | 10/2011 | |
| WO | WO-2006/125207 A2 | 11/2006 | |
| WO | WO 2011116387 A1 * | 9/2011 | ............. C07K 16/00 |

OTHER PUBLICATIONS

Song et al., "Strategic addition of an N-linked glycan to a monoclonal antibody improves its HIV-1-neutralizing activity," Nature Biotechnology vol. 31, No. 11: 1047-1053 (2013).*

(Continued)

*Primary Examiner* — Janet L Andres
*Assistant Examiner* — M. Franco Salvoza
(74) *Attorney, Agent, or Firm* — Clark & Elbing LLP

(57) ABSTRACT

Disclosed herein are glycan-modified anti-CD4 monoclonal antibodies with N-linked glycans attached to the variable region. Expression vectors and cell lines useful for the production of such antibodies, and use of such antibodies for HIV prevention and therapy are also disclosed.

10 Claims, 11 Drawing Sheets

(56) References Cited

U.S. PATENT DOCUMENTS

2015/0165022 A1 6/2015 Loetscher et al.

OTHER PUBLICATIONS

Shirai et al., "H3-rules: identification of CDR-H3 structures in antibodies," FEBS Letters 455: 188-197 (1999).*
Rudikoff et al., "Single amino acid substitution altering antigen-binding specificity," Proc Natl Acad Sci USA 79:1979-1983 (1982).*
Jacquemin, "Variable region heavy chain glycosylation determines the anticoagulant activity of a factor VIII antibody," Haemophilia 16: 16-19 (2010).*
Zheng et al., "The impact of glycosylation on monoclonal antibody conformation and stability," mAbs 3:6: 568-576 (2011).*
Hurez et al. "Anti-CD4 activity of normal human immunoglobulin G for therapeutic use (Intravenous immunoglobulin, IVIg)," Therapeutic Immunology 1: 269-277 (1994).*
Gala et al., "V Region Carbohydrate and Antibody Expression," J Immunol 172: 5489-5494 (2004).*
Endo et al., "Glycosylation of the Variable Region of Immunoglobulin G-Site Specific Maturation of the Sugar Chains," Molecule Immunology vol. 32, No. 13: 931-940 (1995).*
Mimura et al., "Contrasting glycosylation profiles between Fab and Fc of a human IgG protein studied by electrospray ionization mass spectroscopy," Journal of Immunological Methods 326: 116-126 (2007).*
Jefferis, "Glycosylation of Natural and Recombinant Antibody Molecules," Glycobiology and Medicine, John S. Axford (ed.) 143-148 (2005).*
NCBI BLAST Sequence Alignment of SEQ ID Nos. 2, 5)(2017).*
International Search Report for International Application No. PCT/US2013/076051, mailed Mar. 11, 2014 (5 pages).
Written Opinion of the International Searching Authority for International Application No. PCT/US2013/076051, completed Feb. 21, 2014 (6 pages).
Leung et al., "Engineering a unique glycosylation site for site-specific conjugation of haptens to antibody fragments," J Immunol. 154:5919-26 (1995).
Sharkey et al., "Evaluation of a complementarity-determining region-grafted (humanized) anti-carcinoembryonic antigen monoclonal antibody in preclinical and clinical studies," Cancer Res 55:5935s-45s (1995).
Song et al. "Strategic addition of an N-linked glycan to a monoclonal antibody improves its HIV-1-neutralizing activity," Nat Biotechnol. (Abstract) 31(11):1047-52 (2013).
International Preliminary Report on Patentability for International Patent Application No. PCT/US2013/076051, dated Jun. 23, 2015 (7 pages).
Non-Final Office Action for U.S. Appl. No. 14/133,256, dated Aug. 14, 2015 (17 pages).
Ackerman et al., "Natural variation in Fc glycosylation of HIV-specific antibodies impacts antiviral activitiy," J Clin Invest. 123(5):2183-92 (2013).
Wright et al., "Effect of glycosylation on antibody function: implications for genetic engineering," Trends Biotechnol. 15(1):26-32 (1997).
Response to Non-Final Office Action for U.S. Appl. No. 14/133,256, dated Jan. 14, 2016 (7 pages).
Final Office Action for U.S. Appl. No. 14/133,256, dated Jun. 1, 2016 (15 pages).
Notice of Allowance for U.S. Appl. No. 14/133,256, mailed Oct. 21, 2016 (10 pages).
Extended European Search Report for European Patent Application No. 13866337.2, dated Jul. 12, 2016 (15 pages).
Huang et al., "Impact of variable domain glycosylation on antibody clearance: an LC/MS characterization," Anal Biochem. 349(2):197-207 (2006).
Jacobson et al., "Safety, pharmacokinetics, and antiretroviral activity of multiple doses of ibalizumab (formerly TNX-355), an anti-CD4 monoclonal antibody, in human immunodeficiency virus type 1-infected adults," Antimicrob Agents Chemother. 53(2):450-7 (2009).
Pace et al., "Anti-CD4 monoclonal antibody ibalizumab exhibits breadth and potency against HIV-1, with natural resistance mediated by the loss of a V5 glycan in envelope," J Acquir Immune Defic Syndr. 62(1):1-9 (2013).
Tachibana et al., "Building high affinity human antibodies by altering the glycosylation on the light chain variable region in N-acetylglucosamine-supplemented hybridoma cultures," Cytotechnology. 23(1-3):151-9 (1997).
Toma et al., "Loss of asparagine-linked glycosylation sites in variable region 5 of human immunodeficiency virus type 1 envelope is associated with resistance to CD4 antibody ibalizumab," J Virol. 85(8):3872-80 (2011).
Wright et al., "Antibody variable region glycosylation: position effects on antigen binding and carbohydrate structure," The EMBO Journal. 10(10):2717-2723 (1991).
Wu et al., "Structure-based engineering of a monoclonal antibody for improved solubility," Protein Eng Des Sel. 23(8):643-51 (2010).

* cited by examiner

| Symbol | RHPA4259.7 | V5 sequence | number of V5 PNGS | nV5 PNGS position |
|---|---|---|---|---|
| | VK0.16NN | GNDTTNE | 2 | 0.16 |
| | V0.16N | GNDTTKE | 1 | 0.16 |
| | D0.33N | GVNTTKE | 1 | 0.33 |
| | K0.83N | GVDTTNE | 1 | 0.83 |
| | wt | GVDTTKE | 0 | 1 |

Figure 3

30E Gln
67Ser and 65Ser
52Ser, 53Thr and 54Arg
60Asp and 76Ser

Figure 4

SEQUENCE LISTING

```
<160> NUMBER OF SEQ ID NOS: 14

<210> SEQ ID NO 1
<211> LENGTH: 458
<212> TYPE: PRT
<213> ORGANISM: Homo sapiens

<400> SEQUENCE: 1

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125
```

```
Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Phe Gln Lys Ala Ser
        195                 200                 205

Ser Ile Val Tyr Lys Lys Glu Gly Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455

<210> SEQ ID NO 2
<211> LENGTH: 471
<212> TYPE: PRT
<213> ORGANISM: Artificial Sequence
<220> FEATURE:
<223> OTHER INFORMATION: Synthetic or recombinant polypeptide (heavy
      chain of MVI)

<400> SEQUENCE: 2

Met Glu Trp Ser Gly Val Phe Met Phe Leu Leu Ser Val Thr Ala Gly
1               5                   10                  15

Val His Ser Gln Val Gln Leu Gln Gln Ser Gly Pro Glu Val Val Lys
            20                  25                  30
```

-continued

```
Pro Gly Ala Ser Val Lys Met Ser Cys Lys Ala Ser Gly Tyr Thr Phe
            35                  40                  45
Thr Ser Tyr Val Ile His Trp Val Arg Gln Lys Pro Gly Gln Gly Leu
    50                  55                  60
Asp Trp Ile Gly Tyr Ile Asn Pro Tyr Asn Asp Gly Thr Asp Tyr Asp
 65                  70                  75                  80
Glu Lys Phe Lys Gly Lys Ala Thr Leu Thr Ser Asp Thr Ser Thr Ser
                85                  90                  95
Thr Ala Tyr Met Glu Leu Ser Ser Leu Arg Ser Glu Asp Thr Ala Val
            100                 105                 110
Tyr Tyr Cys Ala Arg Glu Lys Asp Asn Tyr Ala Thr Gly Ala Trp Phe
            115                 120                 125
Ala Tyr Trp Gly Gln Gly Thr Leu Val Thr Val Ser Ser Ala Ser Thr
            130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Phe Glu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Ser Ile Glu Lys Thr Ile Ser Lys Ala Lys Gly Gln Pro Arg
            355                 360                 365
Glu Pro Gln Val Tyr Thr Leu Pro Pro Ser Arg Asp Glu Leu Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
            435                 440                 445
```

```
Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 3
<211> LENGTH: 238
<212> TYPE: PRT
<213> ORGANISM: Artificial Sequence
<220> FEATURE:
<223> OTHER INFORMATION: Synthetic or recombinant polypeptide (light
      chain of MVI)

<400> SEQUENCE: 3

Met Glu Trp Ser Gly Val Phe Ile Phe Leu Leu Ser Val Thr Ala Gly
1               5                   10                  15

Val His Ser Asp Ile Val Met Thr Gln Ser Pro Asp Ser Leu Ala Val
            20                  25                  30

Ser Leu Gly Glu Arg Val Thr Met Asn Cys Lys Ser Ser Gln Ser Leu
        35                  40                  45

Leu Tyr Ser Thr Asn Gln Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Val Tyr Tyr
            100                 105                 110

Cys Gln Gln Tyr Tyr Ser Tyr Arg Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 4
<211> LENGTH: 219
<212> TYPE: PRT
<213> ORGANISM: Artificial Sequence
<220> FEATURE:
<223> OTHER INFORMATION: Light chain of Synthetic or recombinant
      polypeptide LM52

<400> SEQUENCE: 4

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Tyr Ser
            20                  25                  30
```

```
Thr Asn Gln Lys Asn Tyr Leu Ala Trp Tyr Gln Gln Lys Pro Gly Gln
         35                  40                  45

Ser Pro Lys Leu Leu Ile Tyr Trp Ala Asn Ser Thr Glu Ser Gly Val
 50                  55                  60

Pro Asp Arg Phe Ser Gly Ser Gly Ser Gly Thr Asp Phe Thr Leu Thr
65                   70                  75                  80

Ile Ser Ser Val Gln Ala Glu Asp Val Ala Val Tyr Cys Gln Gln
                 85                  90                  95

Tyr Tyr Ser Tyr Arg Thr Phe Gly Gly Gly Thr Lys Leu Glu Ile Lys
             100                 105                 110

Arg Thr Val Ala Ala Pro Ser Val Phe Ile Phe Pro Pro Ser Asp Glu
             115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 5
<211> LENGTH: 452
<212> TYPE: PRT
<213> ORGANISM: Artificial Sequence
<220> FEATURE:
<223> OTHER INFORMATION: Synthetic or recombinant polypeptide (heavy
      chain of modified MVI)

<400> SEQUENCE: 5

Gln Val Gln Leu Gln Gln Ser Gly Pro Glu Val Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Arg Gln Lys Pro Gly Gln Gly Leu Asp Trp Ile
        35                  40                  45

Gly Tyr Ile Asn Pro Tyr Asn Asp Gly Thr Asp Tyr Asp Glu Lys Phe
    50                  55                  60

Lys Gly Lys Ala Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Lys Asp Asn Tyr Ala Thr Gly Ala Trp Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Leu His Glu Ala Leu His Ser His Tyr Thr Gln Lys Ser Leu Ser Leu
            435                 440                 445

Ser Pro Gly Lys
    450

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Gly Arg Gly Asn Gln Thr Asp Asn Gln Thr Glu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Gly Arg Gly Asn Gln Thr Asp Asp Gln Thr Glu
```

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Gly Arg Gly Asp Gln Thr Asp Asn Gln Thr Glu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Gly Arg Gly Asp Gln Thr Asp Asp Gln Thr Glu
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Gly Asn Asp Thr Thr Asn Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Gly Asn Asp Thr Thr Lys Glu
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Gly Val Asn Thr Thr Lys Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Gly Val Asp Thr Thr Asn Glu
1               5

```
<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Gly Val Asp Thr Thr Lys Glu
1               5
```

GLYCAN-MODIFIED ANTI-CD4 ANTIBODIES FOR HIV PREVENTION AND THERAPY

CROSS-REFERENCE TO RELATED APPLICATIONS

This application claims benefit of U.S. provisional application No. 61/738,777, filed Dec. 18, 2012 and U.S. provisional application No. 61/864,942, filed Aug. 12, 2013, the disclosures of which are hereby incorporated by reference.

STATEMENT OF GOVERNMENT FUNDING

This invention was made with government support under NIH DA033263 awarded by the NIH. The government has certain rights in the invention.

FIELD OF THE DISCLOSURE

This disclosure generally relates to HIV prevention and treatment. This disclosure also generally relates to glycan modification of antibodies. In particular, this disclosure relates to glycan-modified anti-CD4 antibodies useful for HIV prevention and therapy.

BACKGROUND ART

HIV-1 entry is triggered by interaction of the viral envelope (Env) glycoprotein gp120 with domain 1 (D1) of the T-cell receptor CD4. Ibalizumab (iMab) is a potent and broadly HIV-1neutralizing Ab (Jacobson et al., *Antimicrob. Agents Chemother.* 53:450-457, 2009; Kuritzkes et al., *J. Infect. Dis.* 189:286-291, 2004), which neutralizes HIV by binding mainly to domain 2 (D2) of the CD4 receptor on host T-cells, thus blocking the ability of HIV to use these CD4 receptors to gain entry into T-cells and produce infection (Burkly et al., *J. Immunol.* 149:1779-178, 1992). In a large panel of primary isolates (118 Env pseudotyped viruses) tested recently, ibalizumab neutralized 92% of all viruses as defined by 50% inhibition of infection, and 47.4% of viruses as defined by 90% inhibition of infection. While ibalizumab can potently inhibit a broad range of HIV isolates, a significant fraction of HIV variants can still escape the inhibitory activity of ibalizumab. It has been reported recently that loss of asparagine-linked glycosylation sites in the variable region 5 of HIV type 1 envelope is associated with resistance to ibalizumab (Toma et al., *J. Virology* 85(8): 3872-2880, 2011; Pace et al., *J. Acquir. Immune Defic. Syndr.* Epub ahead of print: September 2012).

Antibodies are glycosylated at conserved positions in their constant regions, and the presence and structure of the carbohydrate attached to the constant region can affect antibody activity (see review by Wright and Morrison, *TIBTECH* 15: 26-32, 1997).

It was reported that the introduction of an N-linked carbohydrate in the heavy chain, not the light chain, resulted in improved solubility (Pepinsky et al., *Protein Sci* 19, 954-966, 2010; Wu, et al., *Protein Eng Des Sel* 23, 643-651, 2010). In Pepinsky, the modification was at the constant region, not the variable region. However, none of previous studies provides the effect of a glycan strategically placed in the variable region of an antibody.

SUMMARY OF THE DISCLOSURE

The present invention provides a new approach for enhancing the activity of monoclonal antibodies through glycan modification in the variable region of the light chain. In various embodiments of the invention, the glycan-modified anti-CD4 monoclonal antibodies, expression vectors and cell lines useful for the production of such antibodies, and use of such antibodies for HIV prevention and therapy are provided.

In one aspect, the present invention provides a glycan-modified anti-CD4 antibody having one or more N-linked glycans attached to the variable region of said antibody. In some embodiments of the invention, the N-linked glycans are attached to the variable region of the light chain of said antibody. The attachment of glycans is achieved through one or more genetically engineered N-linked glycosylation sites in the variable region of said antibody.

In one embodiment of the invention, the glycan-modified anti-CD4 antibody is a modified form of an anti-CD4 antibody having an engineered N-linked glycosylation site in its variable region. In some embodiments, the engineered N-linked glycosylation site is located in the variable region of the light chain of an anti-CD4 antibody, such as wild type (WT) or modified ibalizumab, ibalizumab mutant or modified anti-CD4 antibody. In some specific embodiments, the engineered N-linked glycosylation site is located at an amino acid position of the light chain of ibalizumab or corresponding positions thereof, which is selected from the group consisting of residues 30E, 52, 53, 54, 60, 65 and 67 and 76, and combination thereof. In the present invention, the glycosylation site is at the amino acid position selected from the group consisting of positions 30E Gln, 52Ser, 53Thr, 54Arg, 60Asp, 65Ser, 67Ser, and 76Ser. In some examples, the glycosylation site at 30E Gln, 52Ser, 53Thr, 54Arg, 65Ser, or 67Ser provides improved activity. In one particular example of the invention, the glycosylation site is at position 52Ser.

In one specific example of the invention, the anti-CD4 antibody is a modified form of ibalizumab comprising an engineered N-linked glycosylation site in the variable region of the light chain.

In another specific example of the invention, the glycan-modified anti-CD4 antibody is a modified form of MV1 comprising an engineered N-linked glycosylation site in the variable region of the light chain.

One particular example, the invention provides a glycan-modified anti-CD4 antibody, called as LM52, which is prepared as an IgG 1 antibody with affinity to CD4 (anti-CD4 IgG 1 antibody) modified by an introduction of a N-linked glycan at the position 52.

In another particular example of the invention, a glycan-modified anti-CD4 antibody with improved recycling of the antibody is provided, which has the amino acid sequence of the light chain as set forth in SEQ ID NO: 4, and the heavy chain having the amino acid sequence as set forth in SEQ ID NO: 5.

In some embodiments, the N-linked glycans attached to the antibody are composed of at least 7 carbohydrate units. In other embodiments, the N-linked glycans are composed of 10-11 carbohydrate units.

In additional embodiments of the invention, expression vectors and host cells are provided, which are useful for expressing an anti-CD4 immunoglobulin chain having an engineered N-linked glycosylation site in the variable region.

In a further aspect, the present invention provides a glycan-modified monoclonal antibody having improved activity, in which the glycan-modified anti-CD4 antibody has N-linked glycans attached to the variable region as defined above. The antibody or antigen binding fragment of the invention is effective for inhibiting, treating or/and preventing infection of target cells by human immunodeficiency virus type 1 ("HIV-1").

In a yet aspect, the present invention provides a pharmaceutical composition comprising a therapeutically effective amount of the glycan-modified anti-CD4 antibody of the invention and at least one pharmaceutically acceptable carrier.

In a further yet aspect, the present invention provides a method for inhibiting, treating and/or preventing HIV infection and transmission, which comprises administering a subject in need thereof a pharmaceutical composition comprising a therapeutically effective amount of the glycan-modified anti-CD4 antibody of the invention, and at least one pharmaceutically acceptable carrier.

In another aspect, the present invention provides a glycan-modified monoclonal antibody with improved activity comprising N-linked glycans attached to the variable region of said antibody, particularly in the variable region of the light chain of said antibody.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the embodiments.

In the drawings:

FIG. 3 shows the effect of the introduction of a V5 N-terminal PNGS (SEQ ID NOS: 10-14) on HIV sensitivity to ibalizumab.

FIG. 4 provides an image showing the crystal structure of the ibalizumab-CD4 complex as depicted, indicating several sites in the light chain of ibalizumab which were mutated to introduce an N-linked glycosylation site based on their close distance to the V5 of gp120.

FIGS. 5A and 5B provide a model of glycosylation in V5 of HIV-1 gp120, in the context of both CD4 and ibalizumab (using PyMOL); where the complex was modeled by superimposing the structure of D1 and D2 of CD4 in complex with gp120 (Protein Data Bank accession number 2NXY) onto the same domains of CD4 in complex with ibalizumab (PDB 3O2D); and the glycan (blue) was introduced at the relevant asparagine by superimposing the asparagine with that of a glycan-bound asparagine from PDB 3TYG; and the heavy and L chains of ibalizumab are shown as cyan and magenta ribbons, respectively. The first two domains of human CD4 are green, while HIV-1 gp120 is tan; wherein FIG. 5A shows $Man_5GlcNac_2$ at the position 459 of gp120 in the V5 loop (N-terminal); and FIG. 5B shows $Man_5GlcNac_2$ at the position of 463 of gp120 in the V5 loop (C-terminal).

FIG. 6A shows the ibalizumab L chain mutants (LMs) as constructed, co-transfected into 293A cells with the WT ibalizumab H chain plasmid, purified on a protein-A agarose column, and analyzed by SDS-PAGE (WT ibalizumab was analyzed in the same way).

FIG. 6B shows the purified WT, LM30E, LM53, and LM52 antibodies that were treated with or without PNGase F at denaturing conditions and analyzed by SDS-PAGE.

FIG. 6C shows the N-linked glycoforms on the L chain of LM52 produced in 293A cells that were analyzed by mass spectrometry.

FIG. 6D shows that a positive correlation was observed between the size of the glycan and the neutralization activity.

FIG. 8A shows that LM52 was produced in HEK293A cells with or without tunicamycin (LM52-T) or kifunensine (LM52-K); alternatively, LM52 was produced in the N-acetylglucosaminyltransferase I-negative GnT1(−) HEK293S cells (LM52-G); the purified LM52 proteins, together with unmodified LM52 and WT ibalizumab, were analyzed by SDS-PAGE.

FIG. 8B shows that the neutralization activities of ibalizumab and different glycan variants of LM52 against three ibalizumab-resistant pseudoviruses, as measured in TZM-b1 cells.

FIG. 8C shows that the depiction (using PyMOL) of the space filled by glycans of representative conformations and sizes, when tagged on residue 52 of ibalizumab. Depiction is based on the model generated in FIG. 5 and colors were the same; wherein the 7-ring N-glycan, $Man_5GlcNac_2$, was extracted from PDB entry 3TYG. An 11-ring N-glycan, $Man_3GlcNac_5Fuc$, was extracted from PDB entry 3QUM (these results represent three independent experiments).

FIG. 14A shows the HEp-2 reactivity of LM52 and ibalizumab as measured by ELISA using QUANTA LITE ANA ELISA kit (INOVA Diagnostics); wherein the negative control was an human serum with no antibodies to nuclear and cytoplasmic antigens; and strong and weak positive controls were human sera known to have abundant and small quantities, respectively, of antibodies to nuclear and cytoplasmic antigens.

FIG. 14B shows LM52 and ibalizumab reactivity to single-stranded DNA, double-stranded DNA, insulin, lipopolysaccharide, KLH, and CD4, as measured by ELISA assay; wherein these results were derived from three independent experiments.

DETAILED DESCRIPTION OF THE INVENTION

Figure 1:
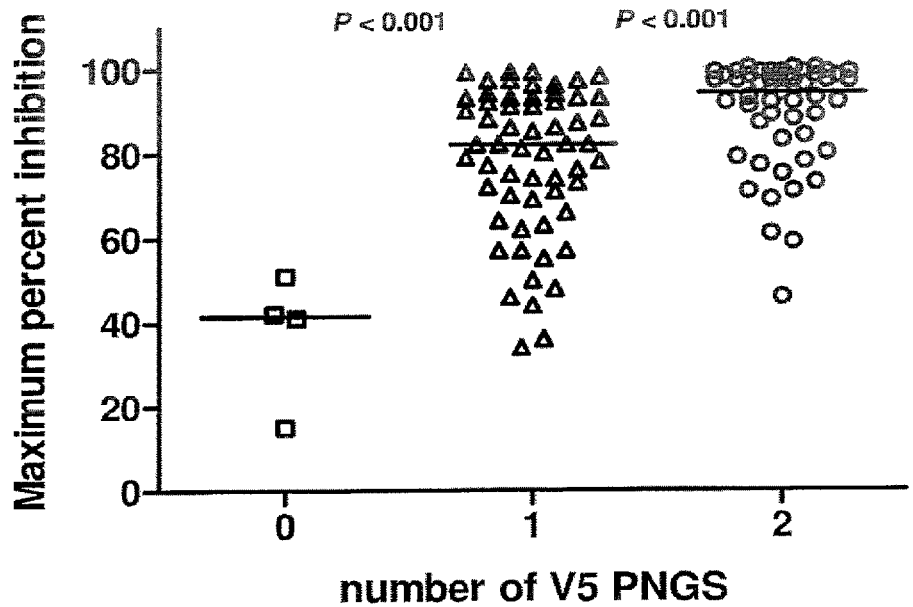
FIG. 1 shows the number of V5 potential N-linked glycosylation sites (PNGS) associated with Ibalizumab resistance (bar indicates median).

The present invention has demonstrated for the first time that the function of a monoclonal antibody can be improved through glycan modification in the variable region. In particular, it has been discovered in the present invention that grafting glycans onto the variable region of the light chain of an anti-CD4 monoclonal antibody can restore a glycan-mediated interaction between the antibody and HIV, such that the antibody with a glycan modification can potently inhibit infection of viral isolates that normally escape the activity of the parent antibody molecule (without the glycan modification).

Accordingly, the present invention provides glycan-modified anti-CD4 monoclonal antibodies, components such as expression vectors and cell lines useful for the production of such antibodies, and use of such antibodies for HIV prevention and therapy.

Definitions

An "antigen" refers to a molecule which contains one or more epitopes and which is capable of eliciting an immunological response. "Antigenic molecules" are also used in a general sense to refer to molecules that are binding targets of the glycan modified proteins disclosed herein.

An "epitope", also known as antigenic determinant, is the portion of an antigenic molecule or molecules that is recognized by the immune system, i.e., B cells, T cells or antibodies. An epitope can be a conformational epitope or a linear epitope. A conformational epitope is formed by discontinuous sections of an antigenic molecule, or formed by multiple molecules. In the case where the antigen is a protein, a conformational epitope can be formed by discontinuous amino acid residues of the same protein molecule, or by amino acid residues on different molecules of the protein (e.g., a quaternary epitope formed by a multimer of the protein). A linear epitope is formed by continuous sections of an antigen, e.g., a continuous sequence of amino acids of a protein antigen.

The term "antibody" is used herein broadly and encompasses intact antibody molecules, which include intact polyclonal, monoclonal, monospecific, polyspecific, chimeric, humanized, human, primatized, single-chain, single-domain, synthetic and recombinant antibodies, and antibody fragments that have a desired activity or function.

The term "antibody fragments," as used herein, includes particularly antigen-binding fragments of an intact antibody. Examples of antigen-binding fragments include, but are not limited to, Fab fragments (consisting of the VL, VH, CL and CH1 domains), Fab' fragments (which differs from Fab fragments by having an additional few residues at the C-terminus of the CH1 domain including one or more cysteines from the antibody hinge region), $(Fab')_2$ fragments (formed by two Fab' fragments linked by a disulphide bridge at the hinge region), Fd fragments (consisting of the VH and CH1 domains), Fv fragments (referring to a dimer of one heavy and one light chain variable domain in tight, non-covalent association which contains a complete antigen recognition and binding site), dAb fragments (consisting of a VH domain), single domain fragments (VH domain, VL domain, VHH domain, or VNAR domain), isolated CDR regions, scFv (or "single chain Fv", referring to a fusion of the VL and VH domains, linked together via a linker), and other antibody fragments that retain antigen-binding function.

The term "variable region" refers to the antigen-binding region of an antibody, which varies greatly between different antibody molecules. The region of an antibody that does not vary the same way and generally engages effector functions of the immune system is called "constant region". Approximately the first 110 amino acids of an immunoglobulin chain (mature form) constitute its variable domain. The two variable domains of the heavy chain (VH) and the two variable domains of the light chain (VL) make up the variable region of an antibody. The six constant domains of the heavy chain ($CH_1$, $CH_2$, and $CH_3$) and the two constant domains of the light chain (CL) make up the constant region of an antibody.

The term "CDR" or "complementarity determining region" refers to the hypervariable regions within the variable domain of an antibody. There are 3 CDRs in each of the heavy chain and light chain variable domains, and are composed of amino acid residues responsible for antigen-binding. The term "framework region" or "FR" refers to the more conserved portions of the variable domains and is composed of residues other than the hypervariable region residues.

The term "antigen-binding site" of an antibody means a conformation and/or configuration formed by amino acids of the antibody to which an antigen binds. For example, the three CDRs of each of the VH and VL domains interact to define an antigen-binding site on the surface of the VH-VL dimer. Together, the six CDRs confer antigen-binding specificity to the antibody. It should be noted, however, a single variable domain (i.e., VH or VL) can also recognize and bind antigen, albeit often less effectively than the whole binding site with all six CDRs.

The term "chimeric antibody" refers to antibodies containing polypeptides from different sources, e.g., different species or different antibody class or subclass. Examples of chimeric antibodies include an antigen-binding portion of a murine monoclonal antibody fused an Fc fragment of a human immunoglobulin. Methods for making chimeric antibodies are known in the art; for example, methods described in patents by U.S. Pat. No. 4,816,397 to Boss et al. and U.S. Pat. No. 4,816,567 to Cabilly et al.

The term "humanized antibody" refers to antibodies that contain non-human sequence elements in a human immunoglobulin backbone or framework. Generally, humanized antibodies are human immunoglobulins (recipient antibody) in which residues from a hypervariable region (CDRs) of the recipient are replaced by residues from a hypervariable region of a non-human species (donor antibody) such as mouse, RAT, rabbit or nonhuman primate having a desired specificity, affinity and capacity. In some instances, framework region (FR) residues of the human immunoglobulin are also replaced by non-human residues. Humanized antibodies may also, in some instances, contain residues that are not found in either the recipient antibody or the donor antibody and introduced to further refine antibody performance. In general, a humanized antibody contains substantially all of at least one, and typically two, variable domains, in which all or substantially all of the hypervariable regions correspond to those of a non-human immunoglobulin and all or substantially all of the framework regions are those of a human immunoglobulin sequence. A humanized antibody optionally also contains at least a portion of an immunoglobulin constant region (Fc), typically that of a human immunoglobulin. Methods for making humanized antibodies are documented in the art; see, for example, by U.S. Pat. No. 5,225,539 to Winter and U.S. Pat. No. 4,816,397 to Boss et al.

The term "non-human primatized antibody" refers to antibodies that contain human sequence elements or non-primate sequence elements in a non-human primate immunoglobulin backbone or framework. For example, non-human primatized antibodies can be made from a non-human primate immunoglobulin (recipient antibody) by replacing residues in a hypervariable region (CDRs) of the recipient antibody with residues from a hypervariable region of a donor antibody from a human or non-primate species such as mouse, RAT or rabbit having a desired specificity, affinity and capacity. Alternatively, non-human primatized antibodies can be made suitable for administration to a desirable primate species by using a recipient immunoglobulin having human or non-primate sequences or sequences from a different primate species and introducing the Fc fragment, and/or residues, including particularly framework region residues, from the desirable primate, into the recipient immunoglobulin. Examples of non-human primatized antibodies include "monkeynized" antibodies disclosed herein in the Examples section.

The term "monospecific antibody" refers to antibodies that recognize and bind to one epitope.

The term "polyspecific antibody" refers to antibodies formed from at least two separate antibodies and binding to multiple (i.e., two or more) separate epitopes.

The term "neutralizing antibody" refers to an antibody that inhibits, reduces or completely prevents HIV-1 infection. Whether an antibody is a neutralizing antibody can be determined by in vitro assays described in the Examples section hereinbelow.

The term "potent neutralizing antibody" refers to an antibody which, when used at a low concentration, reduces HIV-1 infection by at least 50%, 60%, 70%, 80%, 90%, 95%, 99% or greater. Concentrations below 50 µg/ml, between 1 and 50 µg/ml, or even below 1 µg/ml, are considered "low concentrations". In some embodiments, low concentrations are concentrations in the picomolar range, such as 10-900 ng/ml, and include any concentration in that range, such as 800, 700, 600, 500, 400, 300, 200, 100, 75, 50, 25, 10 ng/ml, or even less than 10 ng/ml.

The term "broad neutralizing antibody" refers to an antibody which inhibits HIV-1 infection, as defined by a 50% inhibition of infection in vitro, in more than 50%, 60%, 70%, 80%, 90%, 95%, 99% or greater, of a large panel of (greater than 100) HIV-1 envelope pseudotyped viruses and viral isolates; for example, a large panel of isolates representing envelope diversity by geography, clade, tropism, and stage of infection.

The term "fragment" as used herein refers to a physically contiguous portion of the primary structure of a biomolecule. In the case of proteins, a fragment may be defined by a contiguous portion of the amino acid sequence of a protein and may be at least 3-5 amino acids, at least 6-10 amino acids, at least 11-15 amino acids, at least 16-24 amino acids, at least 25-30 amino acids, at least 30-45 amino acids and up to the full length of the protein minus a few amino acids. In the case of polynucleotides, a fragment is defined by a contiguous portion of the nucleic acid sequence of a polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

A "fusion protein" refers to two or more peptides of different origins connected to each other via a linker or linkers. For example, a fusion protein can include a protein conjugated to an antibody. Other examples include, an antibody conjugated to a different antibody or an antibody conjugated to a Fab fragment. The Fab fragment can be conjugated to the N terminus or C terminus of the heavy or light chain of the antibody, or other regions within the antibody.

A "peptide" is any compound formed by the linkage of two or more amino acids by amide (peptide) bonds, usually a polymer of alpha-amino acids in which the alpha-amino group of each amino acid residue (except the NH2 terminus) is linked to the alpha-carboxyl group of the next residue in a linear chain. The terms peptide, polypeptide and poly (amino acid) are used synonymously herein to refer to this class of compounds without restriction as to size, unless indicated to the contrary. Members of this class having a large size are also referred to as proteins and include antibodies.

Glycan-Modified Anti-CD4 Monoclonal Antibodies

This glycan modification approach disclosed herein is applicable to anti-CD4 monoclonal antibodies, which can be a monoclonal antibody that is a monospecific, polyspecific, chimeric, humanized, human, non-human primatized, single-chain, and/or single-domain antibody. The present approach is also applicable to fragments of anti-CD4 monoclonal antibodies, especially antigen-binding fragments of anti-CD4 monoclonal antibodies.

Anti-CD4 antibodies have been described in the art and can also be readily generated as the protein sequence of the CD4 receptor is available to those skilled in the art. CD4 has four immunoglobulin domains (D1 to D4) that are located on the extracellular surface of the cell, and uses its D1 domain to interact with the $\beta_2$-domain of MHC class II molecules. In some embodiments, the anti-CD4 antibody binds to one or more of D1, D1-D2 junction, D2, the BC or FG loop of D2, or any combination thereof. In specific embodiments, anti-CD4 antibodies used in this disclosure are directed principally to the second immunoglobulin-like domain (D2) (amino acid positions 98-180) of the CD4 receptor. Antibodies directed to the D2 domain of CD4 have the desirable property of blocking HIV infection without interfering with immune functions mediated by interaction of CD4 with the major histocompatibility complex (MHC) class II molecules. In other embodiments, the anti-CD4 antibody used in the present invention binds to an epitope located in the BC-loop of D2 near the D1-D2 junction of the CD4 receptor (amino acids 121-127). In still other embodiments, the anti-CD4 antibody binds to the FG-loop of D2 (amino acids 163-165) and part of D1 (amino acids 77-96). The amino acid numbering corresponds to positions of the mature form of the CD4 receptor, not including the signal peptide. The amino acid sequence of the human CD4 receptor is set forth in SEQ ID NO: 1, in which amino acids 1-25 represent a signal peptide, amino acids 26-122 constitute D1, and amino acids 123-205 constitute D2.

In a specific embodiment, the anti-CD4 monoclonal antibody is the humanized antibody, ibalizumab or "iMab" (previously known as TNX-355, or hu5A8). Ibalizumab potently blocks infection by a broad spectrum of HIV-1 isolates and targets an epitope located in the BC-loop of D2 near the D1-D2 junction of the CD4 receptor, without interfering with immune functions mediated by interaction of CD4 with the major histocompatibility complex (MHC) class II molecules. One example of the anti-CD4 antibody is that provided in U.S. Pat. No. 5,871,732, which is entirely incorporated by reference herein.

In another embodiment, the anti-CD4 antibody or fragment thereof is a mutant of ibalizumab with improved stability. One example is the anti-CD4 antibody having one or more substitutions in the hinge region that prevent intrachain disulfide bond formation resulting in antibody molecules with surprisingly improved bivalent stability, for instance, those provided in WO2008134046 (A1), published on Apr. 27, 2007, which is incorporated herein by reference.

According to the embodiments of the invention, the anti-CD4 antibody may be generated by IgG 4 or IgG 1. In one example of the invention, an anti-CD4 IgG 1 antibody with binding affinity to CD4 was prepared, designated as MV1. The MV1 has a leucine to phenylalanine change at position 234, a leucine to glutamic acid change at position 235 and a proline to serine change at position 331 of the IgG 1 constant region. The MV1 has the amino acid sequences for the heavy chain and light chain as set forth in SEQ ID NOS: 2-3, respectively.

In some examples of the invention, the anti-CD4 antibody may comprise one or more modifications in the Fc region or FcRn region of the heavy chain to improve recycling of the anti-CD4 antibody. One particular example is the anti-CD4 antibody comprises an amino acid sequence of heavy chain as set forth in SEQ ID NO: 5.

Glycan modification disclosed herein involves adding glycans to an engineered N-linked glycosylation site within the variable region of an anti-CD4 antibody. In eukaryotic cells, glycans are attached to asparagine residues within the consensus sequence Asn-X-Ser/Thr of newly synthesized polypeptides as they emerge from the ribosome. This N-linked glycosylation process is an enzyme-directed process which occurs in the ER and the Golgi apparatus. For the purpose of the present invention, the Asn residue within a consensus sequence Asn-X-Ser/Thr is referred to as the "N-linked glycosylation site." The skilled artisan can employ a variety of molecular cloning techniques to engineer an N-linked glycosylation site within the variable region of an anti-CD4 monoclonal antibody, which may include one or more insertions, deletions and/or substitutions of amino acids in order to obtain a consensus N-linked glycosylation sequence Asn-X-Ser/Thr.

In some embodiments, an N-linked glycosylation site is engineered within the V-domain of the light chain (VL) of an anti-CD4 monoclonal antibody. One may consider conducting a 3-D modeling analysis of the relevant antibodies, the CD4 receptor and the HIV gp120 protein to facilitate a determination of a suitable or a more desirable location within the antibody for an N-linked glycosylation site. As illustrated, the present invention demonstrates that for ibalizumab or other anti-CD4 antibody, an N-linked glycosylation site can be introduced to a location that is close to the V5 loop of the HIV gp120 protein bound to CD4 Domain 1 in a 3-D modeling analysis.

In some embodiments, an N-linked glycosylation site is engineered at an amino acid position of the light chain of ibalizumab or corresponding positions thereof, selected from residues 30E, 52, 53, 54, 60, 65 and 67 and 76, and a combination thereof. In particular, the amino acid position is selected from the group consisting of positions 30E Gln, 52Ser, 53Thr, 54Arg, 60Asp, 65Ser, 67Ser, and 76Ser. According to the invention, each of the amino acid changes made to the sequence represented by "30E Gln", "52Ser", "53Thr", "54Arg", "60Asp", "65Ser", "67Ser", and "76Ser" to introduce a new N-linked glycosylation site at each of these positions is given below:

30E Gln: 30E Gln, 31Lys, 32Asn changed to 30E Asn, 31Ala, 32Thr

52Ser: 52Ser, 53Thr, 54Arg changed to 52Asn, 53Ser, 54Thr

53Thr: 53Thr, 54Arg, 55Glu changed to 53Asn, 54Ala, 55Thr

54Arg: 54Arg, 55Glu, 56Ser changed to 54Asn, 55Ala, 56Thr

60Asp: 60Asp, 61Arg, 62Phe changed to 60Asn, 61Ala, 62Thr

65Ser: 65Ser, 66Gly, 67Ser changed to 65Asn, 66Ala, 67Thr

67Ser: 67Ser, 68Gly, 69Thr changed to 67Asn, 68Ala, 69Thr

76Ser: 76Ser, 77Ser, 78Val changed to 76Asn, 77Ala, 78Thr.

In the examples of the invention, a N-linked glycosylation N-linked glycosylation at either or combination of the positions 30EGln, 52Ser, 53Thr, 54Arg, 65Ser and 67Ser can provide an improved activity. In one specific example, the position is position 52Ser. The numbering of these positions is based on the mature form of the light chain (devoid of the first 16 amino acid signal sequence) of ibalizumab, or the corresponding positions thereof. In specific embodiments, the N-linked glycosylation site is engineered at one of 30E Gln, 52Ser, or 53Thr of the ibalizumab light chain. In a particular example, the N-linked glycosylation site is engineered at position 52Ser.

In a particular example of the invention, a derivative IgG1 version of ibalizumab with modifications to improve the stability, called MV1, was used to generate the glycan-modified anti-CD4 antibody. The heavy chain and light chain of the MV1 have the amino acid sequences set forth in SEQ ID NOS: 2 and 3, respectively. The light chain has an engineered N-linked glycosylation site at position 52, which has the amino acid sequence set forth in SEQ ID NO: 4. The MV1 may have a further modification in the Fc region or FcRn region of the heavy chain to improve recycling of the antibody. A particular example of the present invention provides a glycan-modified anti-CD4 antibody with improved activity and stability comprising the amino acid sequence of light chain as set forth in SEQ ID NO: 4 and the amino acid sequence of heavy chain as set forth in SEQ ID NO: 5.

Once an N-linked glycosylation site has been engineered within the variable region of an anti-CD4 monoclonal antibody, glycan-modified forms of such antibody can be readily produced using suitable recombinant expression systems. For example, a cell line suitable for recombinant expression of antibody molecules and capable of N-linked glycosylation can be transfected with expression vector(s) encoding the light chain of an anti-CD4 antibody, wherein at least a variable domain of the light chain has been engineered to include an N-linked glycosylation site. Antibody-containing culture supernatants can be collected and subjected to any appropriate chromatography to obtain a substantially purified antibody preparation.

Cell lines suitable for recombinant expression of antibody molecules are readily available to those skilled in the art, and are generally capable of N-linked glycosylation. In eukaryotes, the N-linked glycosylation process occurs co-translationally and the initial step takes place at the luminal side of the ER membrane, involving the transfer of a $Glc_3Man_9GlcNAc_2$ oligosaccharide to nascent polypeptide chains. This precursor structure is then further modified by a series of glycosidases and glycosyltransferases. Following the removal of the three glucose residues by glucosidase I and II, one specific terminal α-1,2-mannose is removed by mannosidase I. These reactions are well conserved between most lower and higher eukaryotes. At this point, correctly folded $Man_8GlcNAc_2$ N-linked glycosylated proteins may exit the glycosylation machinery; alternatively, they may continue and undergo further species- and cell type-specific processing, catalyzed by a series of enzymes, to produce hybrid and/or complex type glycans. See FIG. 7A. See also review by Wright and Morrison, *TIBTECH* 15: 26-32 (1997); U.S. Pat. No. 6,602,684; and U.S. Pat. No. 7,029,872, for example, which are incorporated herein by reference. In higher eukaryotes, the $Man_8GlcNAc_2$ structures are further trimmed by several α-1,2-mannosidases. The resulting $Man_5GlcNAc_2$ N-linked glycans are subsequently modified by the addition of a β-1,2-linked GlcNAc residue in a reaction catalyzed by GlcNAc transferase I (GnT-I), the resulting $GlcNAcM_8GlcNAc_2$ structure leading ultimately to the formation of "hybrid-type" N-linked glycans. Alternatively, the $GlcNAcM_8GlcNAc_2$ structure is acted on by mannosidase II (Man-II) to move two mannoses, and then by GnT-II to add a second β-1,2-GlcNAc. Glycans with the resulting structure in which both core-α-mannose residues are modified by at least one GlcNAc residue, are called "complex type" N-linked glycans. Additional branching can be initiated by GnT-IV, GnT-V, and GnT-VIs. Galactose and sialic acid residues are further added by galactosyltransferases and sialyltransferases, respectively.

According to this invention, the N-linked glycans added to the variable region of an anti-CD4 antibody should include at least 7, 8, 9, 10, 11 or 12 carbohydrate units or "rings." The term "carbohydrate units" refers to individual saccharide molecules that are linked to each other to make up the native N-glycans in eukaryotic cells; i.e., they include glucose, mannose, N-acetylglucosamine, galactose, and sialic acid. The precise structure (i.e., the compositions and serial linkage) of the N-glycans on an antibody may not be entirely critical as long as the N-glycans include at least 7 units. Examples of N-linked glycans include those typically seen in mammalian cells, e.g., $Man_8GlcNAc_2$ (the GlcNAc at the end being linked to Asn), $Man_5GlcNAc_2$, $GlcNAcMan_5GlcNAc_2$, $GlcNAc_2Man_3GlcNAc_2$, $Gal_2GlcNAc_2Man_3GlcNAc_2$, (sialic acid)$_2$ $GlcNAc_2Man_3GlcNAc_2$, $GalGlcNAcMan_5GlcNAc_2$, as well as the bisected bi-antennary complex, the tri-antennary complex, tri'-antennary complex and tetra-antennary complex N-glycans described in U.S. Pat. No. 6,602,684 (e.g., FIG. 1 therein), incorporated herein by reference.

According to this invention, suitable cells lines for recombinant expression of glycan-modified antibodies are eukaryotic cells, including especially mammalian cell lines such as Chinese hamster ovary (CHO) cells, Baby Hamster Kidney (BHK) cells, (Murine myeloma) NSO cells, Murine myeloma SP2/0 cells, human embryonic kidney 293 (HEK293 or 293) cells, mouse embryonic fibroblast 3T3 cells, and cell lines derived therefrom as long as the derived cells can effectively express a recombinant antibody with N-linked glycosylation. Many of these cells are available through American Tissue Culture Collection (ATCC) or commercial sources. Genetically modified cells that produce glycoproteins having altered glycoforms, e.g., glycoproteins having a particular class of N-linked glycans (such as bi-antennary complex N-linked oligosaccharides) modified with bisecting N-acetylglucosamine (GlcNAc), as described in U.S. Pat. No. 6,602,684, incorporated herein by reference), can also be employed to produce the antibodies of this invention. Other eukaryotic cells which may be appropriate include insect cells and yeast cells, such as baker yeast *S. cerevisiae* and methylotrophic yeast such as *Pichia pastoris*, including particularly yeast strains genetically modified to produce proteins having human N-glycan forms. See, e.g., U.S. Pat. No. 7,029,872, and U.S. Pat. No. 7,449,308, both incorporated herein by reference.

According to the examples of the invention, the N-linked glycans are attached to an antibody molecule produced from cells by treating the antibody molecule isolated from cell culture with enzymes (e.g., PNGase). A shift in the apparent molecular weight of the antibody (which can be detected in SDS-PAGE, Western blot, and the like) as a result of the treatment indicates that N-linked glycans are indeed attached to the antibody molecule. The size of the N-linked glycans can be estimated by comparing with N-linked glycans of known sizes. For a more detailed analysis, the N-linked glycans attached to the antibody can be analyzed by DNA sequencer assisted (DSA), fluorophore assisted carbohydrate electrophoresis (FACE), or MALDI-TOF MS, for example, all of which are techniques well documented in the art. For example, in a DSA-FACE analysis, N-linked glycans are released from a glycosylated antibody peptide: N-glycosidase F (PNGase F). The released N-linked glycans are then derivatized with the fluorophore 8-aminopyrene-1, 3,6-trisulfonate (APTS) by reductive amination. After removal of excess APTS, the labeled N-linked glycans are analyzed with an ABI 3130 DNA sequencer. See, e.g., Laroy et al. (*Nat Protoc.* 1: 397-405 (2006)), U.S. Pat. No. 6,602,684 for MALDI-TOF MS analysis of N-linked glycans on recombinantly produced proteins, which are incorporated by reference herein.

Glycan-modified antibodies can be evaluated in various functional assays to confirm their effectiveness in neutralizing HIV, including assays to determine the breadth and potency of the antibodies against large panels of viral isolates as described in the examples section.

In the embodiments of the invention, it is confirmed that a glycan on the N-terminus of gp120 fills a vacant space between the L chain of ibalizumab and gp120 V5, and ibalizumab's effect on HIV-1 entry is sterically mediated by the mass effect of this glycan. In the tests of a panel of ibalizumab mutants with PNGS at various positions in the L chain on the ability to neutralize HIV-1 infectivity in vitro, it was found that ibalizumab mutants bearing a glycan located in close proximity to V5 in the ibalizumab-CD4-gp120 complex efficiently neutralized HIV-1. These ibalizumab mutants also neutralized HIV-1 strains that are resistant to wild-type ibalizumab. In one particular example of the invention, an ibalizumab mutant, LM52, neutralized 100% of the tested 118 HIV-1 isolates at a potency more than 10-fold higher than wild-type ibalizumab judging by the geometric mean $IC_{80}$, the antibody concentration required to neutralize 80% of infection. It is indicated that ibalizumab blocks HIV-1 entry through a steric hindrance mechanism, and provide an example of how a strategic placement of an N-linked glycosylation site can be used to improve the activity of a monoclonal antibody.

Based on the findings in the invention, it is indicated that the glycan-addition approach may be adapted to enhance their functional activity of monoclonal antibodies. Using the structural-activity relationship (SAR), it is conceivable that increasing the bulk at key positions on the antibody could lead to improved activity so as to generate a superior monoclonal antibody product.

In some embodiments of this invention, it may be desirable to produce antibodies with substantially homogeneous N-linked glycans or one class of N-linked glycans. By "substantially homogeneous" it is meant that at least 50%, 60%, 75%, 80%, 85%, 90% or even 95% of the N-linked glycans on the antibody molecules in a preparation are of the same structure, same size (i.e., same molecular weight, or alternatively, same number of carbohydrate "rings"), or same range of size (e.g., 9-12 "rings", or 10-11 "rings"), and/or type. This can be achieved by utilizing cell lines genetically engineered to express or overexpress a selected set of enzymes involved in N-glycosylation (see, e.g., U.S. Pat. No. 6,602,684 and U.S. Pat. No. 7,029,872, incorporated by reference herein), or to disrupt an enzyme at an intermediate stage in the N-glycosylation pathway (e.g., GnT1 knockout strains), or to utilize one or more inhibitors that target specific processing enzymes, or a combination thereof. Examples of inhibitors include Kifunensine, DMJ (for "deoxymannojirimycin"), and Swainsonine.

Pharmaceutical Composition

Pharmaceutical composition comprising a glycan-modified antibody disclosed herein can be prepared by mixing the antibody with one or more optional pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, antioxidants including ascorbic acid and methionine, chelating agents such as EDTA; salt forming counter-ions such as sodium; non-ionic surfactants such as TWEEN™, PLURONICS™ or polyethylene glycol (PEG), or combinations thereof.

The pharmaceutical composition can contain more than one active compound, e.g., one or more antibodies, in combination with one or more additional beneficial compound for inhibiting, preventing and treating HIV infections.

The active ingredients can be combined with the carrier in any convenient and practical manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

Methods of Treatment and Prevention

In a further aspect, the glycan modified antibodies disclosed herein, optionally provided in pharmaceutically acceptable carrier, are employed for the treatment and prevention of HIV infection in a subject, as well as prevention of HIV transmission.

The term "treatment" of HIV infection refers to effective inhibition of the HIV infection so as to delay the onset, slow down the progression, reduce viral load, and/or ameliorate the symptoms caused by HIV infection.

The term "prevention of HIV infection" means the onset of HIV infection is delayed, and/or the incidence or likelihood of HIV infection is reduced or eliminated.

The term "prevention of HIV transmission" means the incidence or likelihood of HIV being transmitted from one individual to another (e.g., from an HIV-positive woman to the child during pregnancy, labor or delivery, or breastfeeding; or from an HIV-positive subject to an HIV-negative partner) is reduced or eliminated.

The term "subject" refers to any primate subject, including human and non-human subjects (e.g., rhesus subjects).

To inhibit, treat and/or prevent HIV infection, a therapeutically effective amount of a glycan-modified antibody disclosed herein is administered to a subject in need.

The term "therapeutically effective amount" means the dose required to effect an inhibition of HIV infection so as to treat and/or prevent HIV infection. The dosage of an antibody depends on the disease state and other clinical factors, such as weight and condition of the subject, the subject's response to the therapy, the type of formulations and the route of administration. The precise dosage to be therapeutically effective and non-detrimental can be determined by those skilled in the art. As a general rule, a suitable dose of an antibody for the administration to adult humans parenterally is in the range of about 0.1 to 20 mg/kg of patient body weight per day, once a week, or even once a month, with the typical initial range used being in the range of about 2 to 10 mg/kg. Since the antibodies will eventually be cleared from the bloodstream, re-administration may be required. Alternatively, implantation or injection of antibodies provided in a controlled release matrix can be employed.

The antibodies can be administered to the subject by standard routes, including the oral, transdermal or parenteral (e.g., intravenous, intraperitoneal, intradermal, subcutaneous or intramuscular). In addition, the antibodies can be introduced into the body, by injection or by surgical implantation or attachment such that a significant amount of a desirable antibody is able to enter blood stream in a controlled release fashion.

Sequence Listing

SEQ ID NO: 1: the amino acid sequence of the human CD4 receptor (amino acids 1-25 representing a signal peptide, amino acids 26-122 constituting D1, and amino acids 123-205 constituting D2):

MNRGVPFRHLLLLVLQLALLPAATQGKKVVLGKKGDTVELTCTASQKKS

IQFHWKNSNQIKILGNQGSFLTKGPSKLNDRADSRRSLWDQGNFPLIIK

NLKIEDSDTYICEVEDQKEEVQLLVFGLTANSDTHLLQGQSLTLTLESP

PGSSPSVQCRSPRGKNIQGGKTLSVSQLELQDSGTWTCTVLQNQKKVEF

KIDIVVLAFQKASSIVYKKEGEQVEFSFPLAFTVEKLTGSGELWWQAER

ASSSKSWITFDLKNKEVSVKRVTQDPKLQMGKKLPLHLTLPQALPQYAG

SGNLTLALEAKTGKLHQEVNLVVMRATQLQKNLTCEVWGPTSPKLMLSL

KLENKEAKVSKREKAVWVLNPEAGMWQCLLSDSGQVLLESNIKVLPTWS

TPVQPMALIVLGGVAGLLLFIGLGIFFCVRCRHRRRQAERMSQIKRLLS

EKKTCQCPHRFQKTCSPI

SEQ ID NO: 2: the amino acid sequence of the heavy chain of MV1 (471 amino acids, including the first 19 amino acid residues constituting a leader sequence):

MEWSGVFMFLLSVTAGVHSQVQLQQSGPEVVKPGASVKMSCKASGYTFT

SYVIHWVRQKPGQGLDWIGYINPYNDGTDYDEKFKGKATLTSDTSTSTA

-continued

```
YMELSSLRSEDTAVYYCAREKDNYATGAWFAYWGQGTLVTVSSASTKGP

SVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCD

KTHTCPPCPAPEFEGGPSVFLFPPKPKDTLMISRTPEVTCVVVDVSHED

PEVKFNWYVDGVEVHNAKTKPREEQYNSTYRVVSVLTVLHQDWLNGKEY

KCKVSNKALPASIEKTISKAKGQPREPQVYTLPPSRDELTKNQVSLTCL

VKGFYPSDIAVEWESNGQPENNYKTTPPVLDSDGSFFLYSKLTVDKSRW

QQGNVFSCSVMHEALHNHYTQKSLSLSPGK*
```

SEQ ID NO: 3: the amino acid sequence of the light chain of MV1 (238 amino acids, including the first 19 amino acids which constitute a leader sequence):

```
MEWSGVFIFL LSVTAGVHSD IVMTQSPDSL AVSLGERVTM

NCKSSQSLLY STNQKNYLAW YQQKPGQSPK LLIYWASTRE

SGVPDRFSGS GSGTDFTLTI SSVQAEDVAV YYCQQYYSYR

TFGGGTKLEI KRTVAAPSVF IFPPSDEQLK SGTASVVCLL

NNFYPREAKV QWKVDNALQS GNSQESVTEQ DSKDSTYSLS

STLTLSKADY EKHKVYACEV THQGLSSPVT KSFNRGEC
```

SEQ ID NO: 4: the amino acid sequence of the Light chain of LM52:

```
DIVMTQSPDSLAVSLGERVTMNCKSSQSLLYSTNQKNYLAWYQQKPGQS

PKLLIYWANSTESGVPDRFSGSGSGTDFTLTISSVQAEDVAVYYCQQYY

SYRTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

SEQ ID NO: 5—the amino acid sequence of the heavy chain of a modified MV1 with improved recycling of the antibody (452 amino acids with two modifications):

```
QVQLQQSGPEVVKPGASVKMSCKASGYTFTSYVIHWVRQKPGQGLDWIG

YINPYNDGTDYDEKFKGKATLTSDTSTSTAYMELSSLRSEDTAVYYCAR

EKDNYATGAWFAYWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPEFEGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPASIEKTISK

AKGQPREPQVYTLPPSRDELTKNQVSLTCLVKGFYPSDIAVEWESNGQP

ENNYKTTPPVLDSDGSFFLYSKLTVDKSRWQQGNVFSCSVLHEALHSHY

TQKSLSLSPGK*
```

The description of some specific embodiments provides sufficient information that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

EXAMPLES

Materials and Methods

1. Cell Lines, Reagents, and Pseudotyped Viruses

TZM-b1 cells (catalog no. 8129) were obtained through the AIDS Research and Reference Reagent Program (AR-RRP), Division of AIDS, NIAID, NIH. This is a genetically engineered HeLa cell line that expresses CD4, CXCR4, and CCR5 and contains Tat-responsive reporter genes for luciferase and β-galactosidase under the control of an HIV-1 long terminal repeat. The Standard Reference Panels of Subtype B HIV-1 Env clones from acute and early infections and Env-deficient backbone plasmid (SG3ΔEnv) were also obtained through the NIH ARRRP. HIV-1 env pseudotyped viruses were prepared by co-transfection of 293A cells (Invitrogen) with an Env-expression plasmid and SG3ΔEnv. Recombinant sCD4 comprising the full-length extracellular domain of human CD4 was obtained from Progenics Pharmaceuticals, Inc. (Tarrytown, N.Y.). Ibalizumab protein was provided by TaiMed Biologics (Irvine, Calif.). Plasmids pMV1 and pLC, which encode for ibalizumab H chain and L chain, respectively, were amplified from cDNA and cloned into pCDNA3.1 (+) (Invitrogen). N-acetylglucosaminyl-transferase I-negative GnT1(−) human embryonic kidney (HEK) 293S cells were obtained from ATCC (catalog no. CRL-3022).

2. Addition of N-Linked Glycosylation Sites to the Anti-CD4 Antibody L Chain

The Asn-Ala-Thr (LM30E, LM53, LM54, LM60, LM65, LM67, and LM76) or Asn-Ser-Thr (LM52) sequences were introduced by mutagenesis to create mutants at the light (L) chain of the anti-CD4 antibody such as WT ibalizumab or MV1. Mutagenesis was carried out with QUICKCHANGE mutagenesis kit (Stratagene, Santa Clara, Va.). The L (light) chain mutants (LM) constructs were generated from anti-CD4 IgG1 antibodies (such as MV1), and then were sequenced and transiently transfected into HEK293A cells (1:1 ratio of heavy and L chain plasmids) with polyethylenimine (PEI)-DNA complex. Supernatants were harvested on day 5 post transfection and LM proteins were purified with a protein-A agarose (Thermo Scientific, Rockford, Ill.) column. WT ibalizumab and LM30E, LM52, and LM53 were treated with PNGase F (New England Biolabs, Ipswich, Mass.) under denaturing conditions, before analysis by SDS-PAGE.

3. Virus Neutralization Assay Using TZM-b1 Cells

Neutralization assay was performed based on the method of Wei et al.[37] with modifications[38]. Briefly, 10,000 cells per well were seeded in a 96-well plate in 100 μL/well of DMEM supplemented with 10% fetal bovine serum (D10) and incubated overnight. The next day, serially diluted ibalizumab or LM proteins were added to the cells and incubated for 1 h. Then, 200×50%-tissue-culture-infective-doses ($TCID_{50}$) of replication-competent or pseudotyped HIV-1 were prepared in D10 containing DEAE-Dextran (Sigma, St. Louis, Mo.) and added to the cells. The cells were incubated for 48 h and β-galactosidase activity was measured using the Galacto-Star System (Applied Biosystems, Cedarville, Ohio). The percentage of inhibition of viral infectivity was calculated as 1 minus the ratio of antibody-treated wells versus untreated-infected wells multiplied by 100. The $IC_{50}$ and $IC_{80}$ values (the antibody concentrations that confer 50% and 80% neutralization, respectively) were calculated by a non-linear regression analysis.

4. Surface Plasmon Resonance

Binding affinity analyses were performed with a BIA-CORE T3000 optical biosensor (GE Healthcare, Piscataway, N.J.). Immobilization of ibalizumab and all the glycan variants were performed following the standard amine coupling procedure. Briefly, carboxyl groups on the sensor chip surface were activated by injection of 35 μL of a solution containing 0.2 M N-(3-dimethylaminopropyl)-N-ethylcarbodiimide and 0.05 M Nhydroxysuccinimide at a flow rate of 5 μL/minute. Next, ibalizumab or its mutant variant, at a concentration of 2 μg/mL in 10 mM sodium-acetate buffer, pH 4.5, was allowed to flow over the chip surface at a rate of 10 μL/minute until the desired level of response units of reacted protein (150-200 RU) was achieved. After unreacted protein was washed out, excess active ester groups on the sensor surface were capped by the injection of 35 μL of 1 M ethanolamine, pH 8.0, at a flow rate of 5 μL/minute. As background to correct instrument and buffer artifacts, a reference was generated under the same conditions with omission of the protein ligand. Binding experiments were performed at 25° C. in HBS-EP buffer (0.01 M HEPES, 0.15M NaCI, 3 mM EDTA, 0.005% vol/vol surfactant P20 (GE Healthcare). Binding kinetics were measured by passing various concentrations of analyte (human sCD4 protein) over the chip surface at a flow rate of 30μL/minute for 3 min. Dissociation of bound analytes was monitored while the surface was washed for 10 min. Remaining analytes were removed at a flow rate of 50 μL/minute with two 30-sec injections of 10 mM glycine-HCI, pH 2.0. For kinetics data analysis, the kinetic parameters were determined by collectively fitting the overlaid sensograms locally using the BIAevaluation 4.1 software to the 1:1 Langmuir binding model.

5. Identification of N-Linked Glycosylation on LM52

Three micrograms of LM52 protein was dissolved in 50 mM ammonium bicarbonate (ABC)/50% tetrafluoroethylene and reduced by adding 40 mM dithiothreitol (DTT). After incubation at 65° C. for 1 h, the protein samples were processed for alkylation by adding 40 mM iodoacetamide and incubating at room temperature for 1 h in the dark. The reaction was quenched by adding 40 mM DTT followed with 1 h incubation. Then 25 mM ABC was added before trypsin digestion. Protein samples were then treated with 0.2 μg trypsin (Promega) for overnight. The digested protein samples were dried and re-dissolved with 20 μL of water before LC-MS/MS analysis. For the assignment for N-glycans on antibodies, the measured masses of trypsin-digested antibody were compared to a database that combined predicted tryptic peptides and N-linked glycans. The assigned glycopeptides were confirmed by the appearance of glycan fragments in MS/MS spectra. For PNGasc digestion, LM52 was treated with PNGase F (New England Biolabs) overnight.

6. Statistical Analyses

Differences in antibody potencies shown in Figures S2 and S3 were assessed by parametric (Students paired t-test) analyses of 50% and 80% inhibitory concentrations, using GraphPad Prism v5.03 software. Statistical significance was achieved if P≤0.05.

Results

Example 1

Sequence analysis of a panel of 118 viral isolates suggests that ibalizumab resistance was associated with the number of potential N-linked glycosylation sites (PNGS) in the V5 loop of gp120 (Pace et al., *J. Acquir. Immune Defic. Syndr.* Epub ahead of print: Sep. 2012). As shown in FIG. 1, viruses having two N-linked glycosylation sites in V5 were sensitive to ibalizumab, whereas viruses having no N-linked glycosylation site in V5 were resistant. Bar indicates median. Interestingly, clinical viral isolates that have developed resistance to ibalizumab monotherapy also display a loss in a potential V5 glycosylation site (Toma et al., *J. Virology* 85(8): 3872-2880, 2011).

Figure 2:
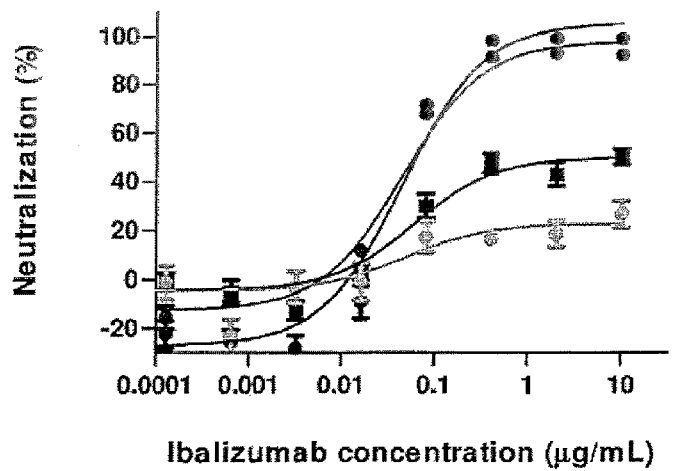
FIG. 2 shows the loss of V5 N-terminal PNGS (SEQ ID NOS: 6-9) conferring HIV resistance to ibalizumab.

One wild-type virus (AC10.0.29) in the panel has two N-linked glycosylation sites in V5 and is naturally sensitive to ibalizumab. The V5 N-linked glycosylation sites in this virus were systematically deleted using site-directed mutagenesis, and the resulting mutant viruses became resistant to ibalizumab (see FIG. 2).

Another wild-type virus (RHPA4259.7) in the panel has no N-linked glycosylation site in V5 and is naturally resistant to ibalizumab. This virus was modified to systematically add N-linked glycosylation sites in V5. As shown in FIG. 3, the resulting mutant viruses became sensitive to ibalizumab.

Analysis of superimposed crystal structures of ibalizumab, CD4 and HIV gp120 revealed that the V5 loop of gp120 is adjacent to the interaction site between the light chain of ibalizumab and CD4. Additional modeling analysis suggested that ibalizumab may normally inhibit HIV through steric hindrance, and that loss of a glycan on gp120 V5 may allow a virus to bypass this steric hindrance and escape the anti-HIV activity of ibalizumab. It was hypothesized in the present invention that addition of N-linked glycan sites onto ibalizumab at a region that is close to the gp120 V5 (for example near the N-terminus of V5) may allow the modified ibalizumab to neutralize viruses that are normally resistant to ibalizumab. The following experiments were conducted to verify this hypothesis.

Based on the crystal structure of the ibalizumab-CD4 complex, several sites in the light chain of ibalizumab were selected based on their putatively close distance to the V5 of gp120. These include amino acid positions 30E, 67, 65, 52, 53, 54, 60, and 76—the numbering is based on the mature version of the light chain absent the 19 amino acid signal sequence (i.e., a leader sequence) and following the Kabat and Chothia Numbering Scheme which accounts for amino acid residues not accounted for in the original numbering. For example, position "30E" refers to the $5^{th}$ amino acid in a stretch of amino acids (30A, 30B, 30C, 30D, 30E, . . . ) between the positions originally numbered as 30 and 31. Potential N-linked glycosylation sites were introduced at each of these positions. The mutant light chains all had higher molecular weights than the wild type light chain, suggesting the presence of an added glycan in these mutants. When the mutant light chains were treated with the deglycosylation agent, PNGase F, their molecular weights dropped to that of a normal ibalizumab wild type light chain.

These data confirmed that N-linked glycosylation sites were indeed added to the mutant light chains.

Example 2

Design of Ibalizumab Variants

Studies of ibalizumab-resistant HIV-1 strains revealed that resistance is mainly conferred by the loss of glycan(s) from the V5 loop of HIV-1 Env gp120. To further explore the role of V5 glycosylation in ibalizumab susceptibility, we modeled the interactions between gp120, CD4 and ibalizumab using the structures reported to the Protein Data Bank (accession number 2NXY and 302D). The V5 N-terminal glycan is situated closest to the ibalizumab L chain (FIG. 5A), while the V5 C-terminal glycan is further away from ibalizumab (FIG. 5B). This model raises the possibility that the fit of the N-terminal glycan into the space between gp120 and ibalizumab exerts a mass effect on gp120, thereby disrupting its conformational changes (twists and turns) that are essential for HIV-1 entry into the target cell. This model also suggests that introduction of a similarly sized glycan into the ibalizumab L chain may boost its ability to inhibit entry of HIV-1 strains that have lost their V5 N-terminal glycan.

Figure 6:
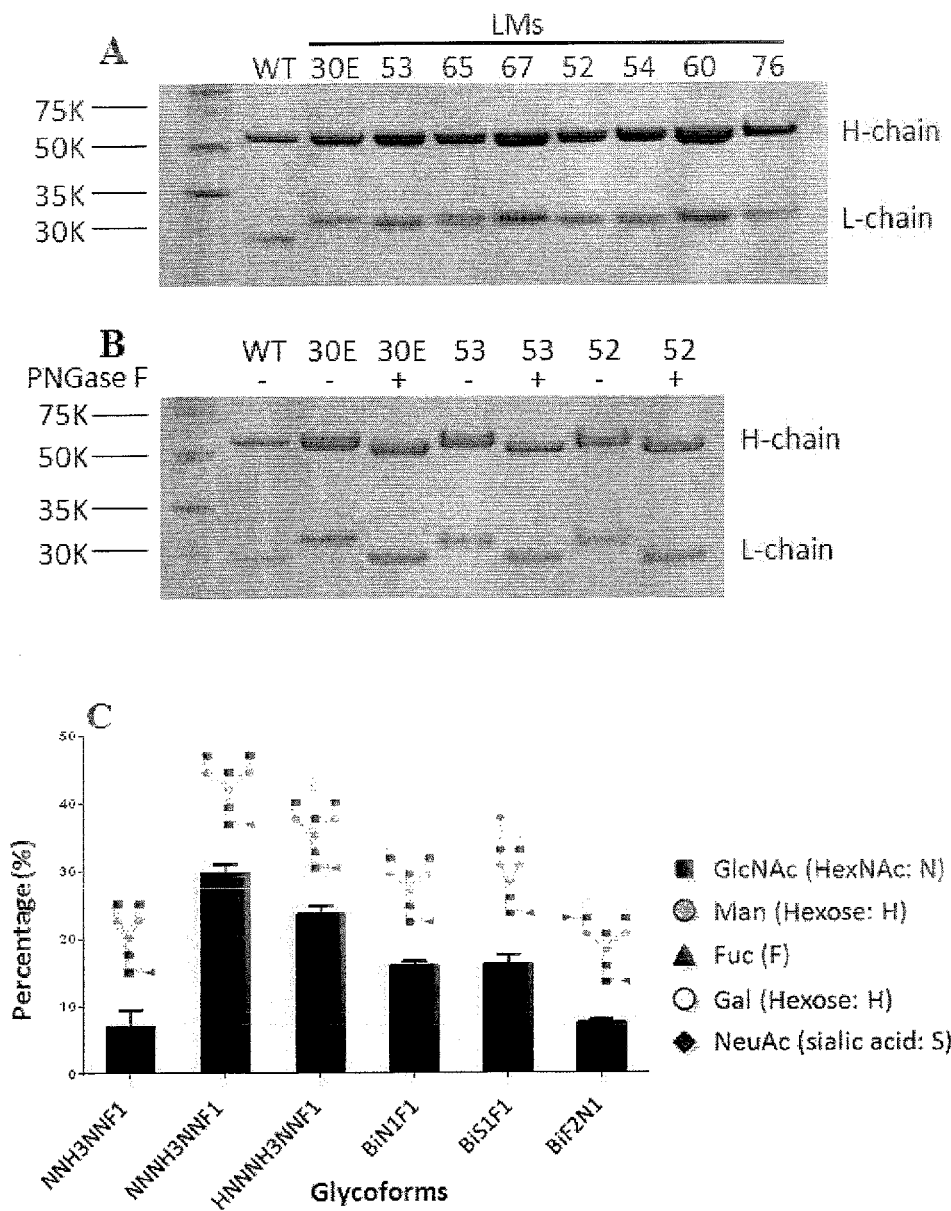
FIGS. 6A-6D show the N-linked glycosylation in the L chain of ibalizumab; where.
Figure 6:
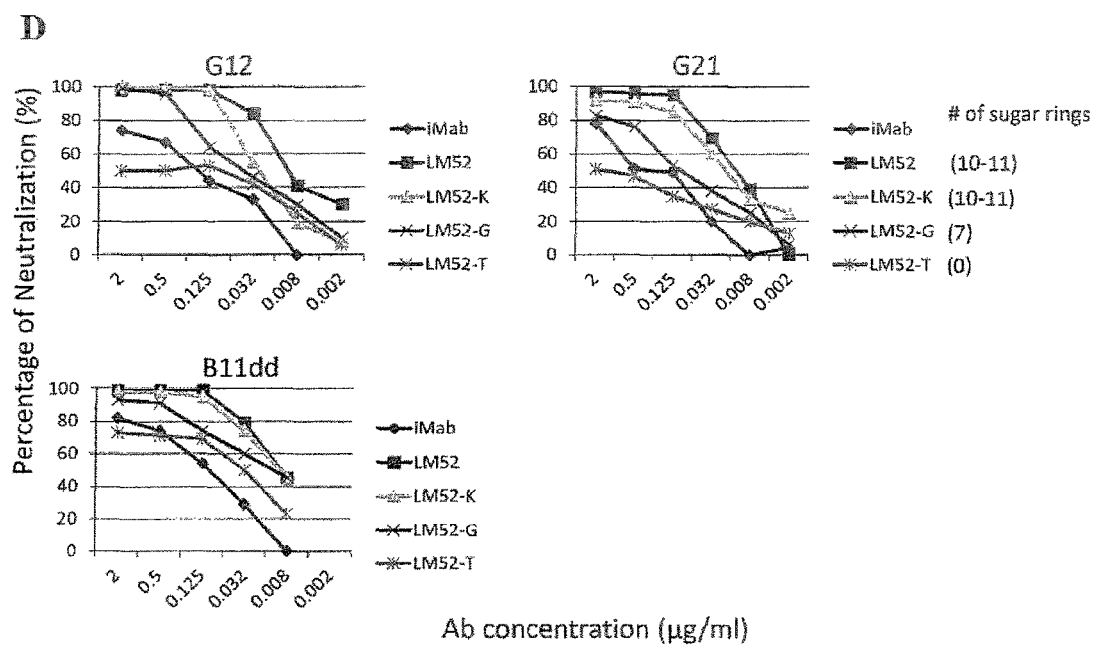

We therefore introduced PNGS into residues (30E, 52, 53, 54, 60, 65, 67, and 76) in the variable region of the ibalizumab L chain that are proximal to the V5 loop of gp120. These ibalizumab L chain mutants (LMs) were constructed, sequenced, and transfected into 293A cells to produce mutant proteins. We purified the variant mAbs by protein-A agarose chromatography, and analyzed them by SDS-PAGE (FIG. 6A). Yields of LMs from transient expression in 293A cells were comparable to those of wild-type ibalizumab. A slightly bigger L chain was observed in each of the LMs compared to the wild-type L chain. To confirm that the larger sizes are due to glycosylation, LMs 30E, 52, and 53 were treated with PNGase F under denaturing conditions and analyzed by SDS-PAGE (FIG. 6B). As expected, the sizes of the L chains of these variants post-PNGase F treatment were decreased to the size of the wild-type. We next used mass spectrometry to identify the form of N-glycans introduced to the L chain of LM52 routinely produced in 293A cells. Over six forms of complex type N-glycans with 8-12 rings were identified on the L chain, with 80% of these forms having 9-11 rings (FIG. 6C). The LM52 mutants, differing only in their glycan sizes, were tested in neutralization assays. Higher neutralization activities were observed with LM52 mutant proteins with bigger N-linked glycans in all of the three viruses tested (FIG. 6D). Taken together, these data confirmed that N-linked glycans were introduced into the desired residues of the ibalizumab L chain.

Example 3

CD4 Binding and HIV-1 Neutralization by LMs

We next evaluated the kinetics of binding of these ibalizumab LMs to human soluble CD4 (sCD4) by surface plasmon resonance. In a Biacore assay using sCD4 as the analyte, WT ibalizumab and LMs bound sCD4 with similar binding kinetics. The $K_D$ of six of these LMs bound to sCD4 was in the range of 0.19 nM to 0.8 nM (Table 1), and these numbers were within 2-fold of the $K_D$ of wild-type ibalizumab (0.43 nM). These data showed that the addition of an N-linked glycan at these select locations in the L chain of ibalizumab did not markedly affect its ability to bind CD4.

TABLE 1

The binding kinetics of ibalizumab and its LMs to human CD4

| Antibody | $K_{on}$ ($10^5$/Ms) | $K_{off}$ ($10^{-5}$/s) | $K_D$ (0.1 nM) |
|---|---|---|---|
| ibalizumab | 2.8 | 12 | 4.3 |
| LM30E | 1.1 | 15 | 14 |
| LM52 | 4.6 | 16 | 3.5 |
| LM53 | 2.9 | 13 | 4.5 |
| LM54 | 3.7 | 27 | 7.3 |
| LM60 | 4.4 | 8.3 | 1.9 |
| LM65 | 3.3 | 49 | 15 |
| LM67 | 2.5 | 20 | 8 |
| LM76 | 5.0 | 14 | 2.8 |

Figure 7:
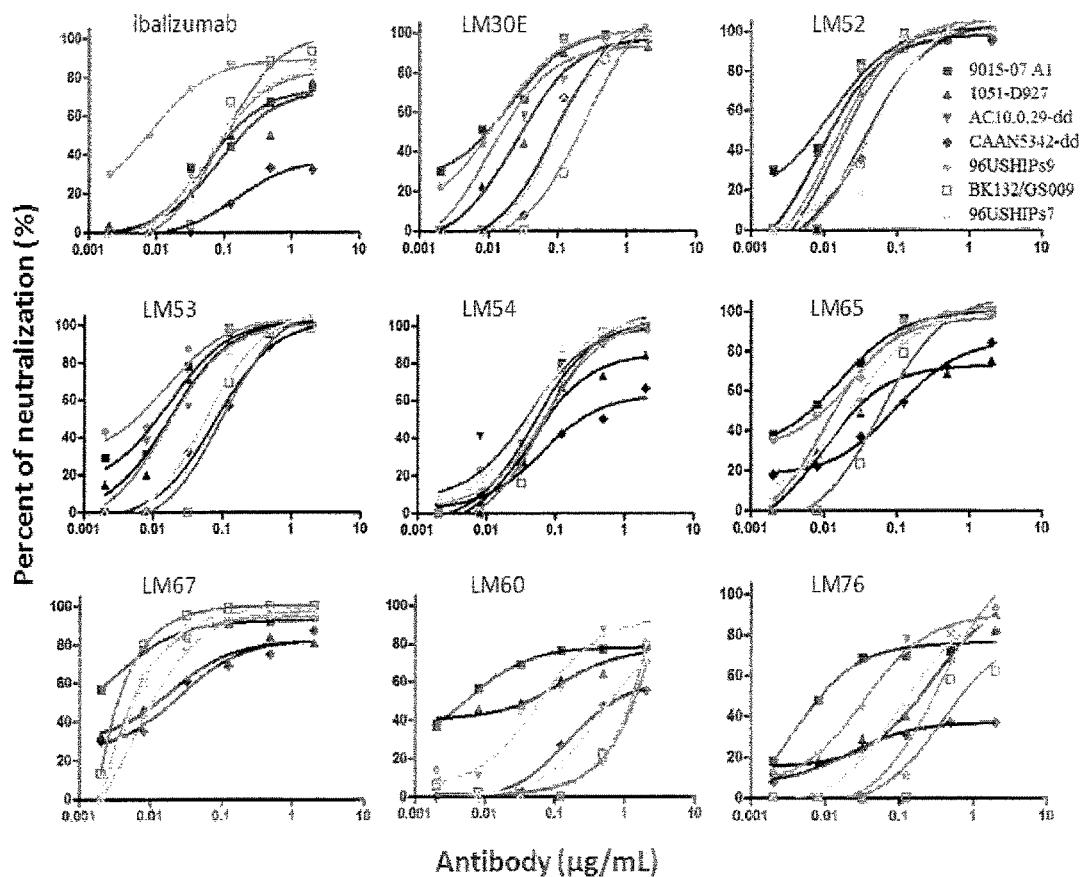
FIG. 7 shows the neutralization activities of WT ibalizumab and its LMs; wherein neutralization against a panel of ibalizumab-resistant or partially ibalizumab-resistant pseudovirus or replication-competent HIV-1 strains was measured by TZM-b1 assay; 96USHIPs9, BK132/GS009, and 96USHIPs7 were replication-competent; CAAN5342.A2-dd and AC10.0.29-dd were site-directed Env mutants without any PNGS in V5 and were resistant or partially resistant to neutralization by wild-type ibalizumab; 9015-07 A1 and 1051-D927 were clade B transmitted founder viruses (data represent three independent experiments).

We next explored the HIV-1 neutralizing capacity of the LMs compared to WT ibalizumab. To this end, we tested the LMs against a panel of HIV-1 viruses that are resistant or partially resistant to ibalizumab, including 3 replication-competent HIV-1 strains (FIG. 7). Using this panel of ibalizumab-resistant viruses, an average MPI of 75% and $IC_{80}$ of 1.43 µg/mL were observed when WT ibalizumab was tested up to 2 µg/mL. Markedly improved neutralization activities were observed for four LMs (LM30E, LM52, LM53, and LM67), with an average MPI of 91-99% and $IC_{80}$ of 0.05-0.14 µg/mL (FIG. 7 and Table 2). Among these, LM52 appears to have the best HIV-1 neutralization potency. Two other variants (LM54 and LM65) yielded more modest improvement in virus-neutralization activities compared to ibalizumab. Interestingly, the PNGS in the six LMs that showed improved HIV-1 neutralizing activity are also closer to V5 (459) of gp120 (Table 2) than the PNGS in LM60 and LM76, which showed HIV-1 neutralizing activity comparable to those of WT ibalizumab. Therefore, it seems that positioning the N-glycan closer to V5 improves the neutralization profile of ibalizumab variants. We note, however, that the orientation of the glycan, in addition to the distance to V5, may also play a critical role.

TABLE 2

Comparison of ibalizumab and its light chain mutants

| | WT | LM30E | LM52 | LM53 | LM54 | LM65 | LM67 | LM60 | LM76 |
|---|---|---|---|---|---|---|---|---|---|
| Mean MPI (%) | 75 | 98 | 98 | 99 | 93 | 93 | 91 | 75 | 78 |
| Distance (Å) to V5 | | 11.1 | 19.8 | 19.8 | 23.3 | 21.3 | 18.9 | 27.6 | 31.2 |
| $IC_{80}$ (µg/mL) Geometric mean | 0.87 | 0.14 | 0.05 | 0.09 | 0.28 | 0.20 | 0.05 | 1.5 | 0.75 |

Example 4

Glycan Size Influences LM52 Activity

Figure 8:
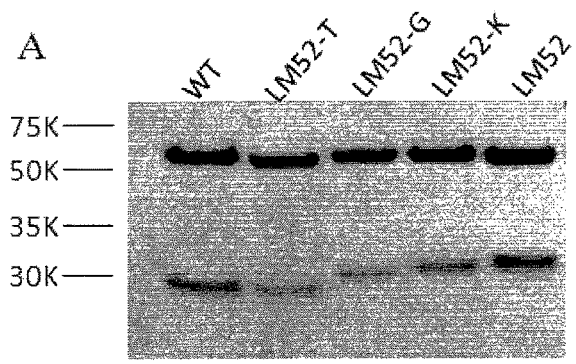
FIGS. 8A-8C show the influence of glycan size on the HIV-1 neutralization activity of LM52, where.
Figure 8:
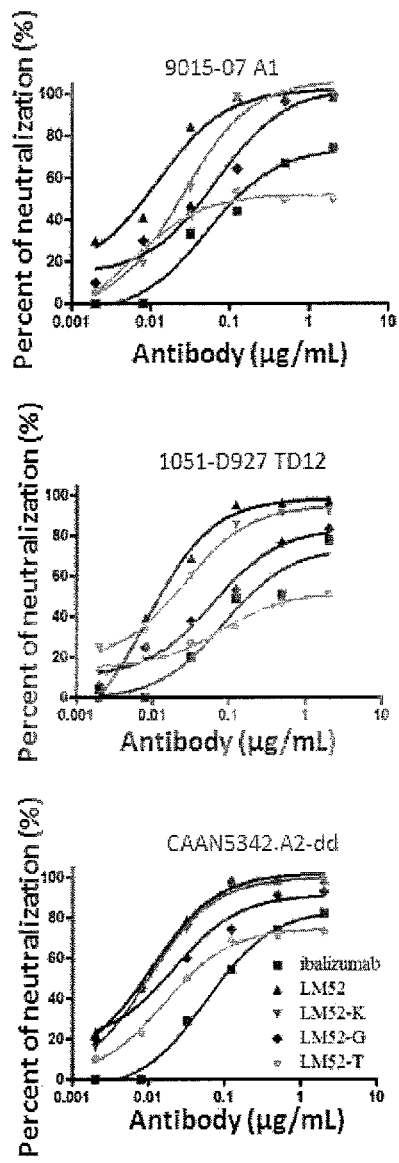
Figure 8:
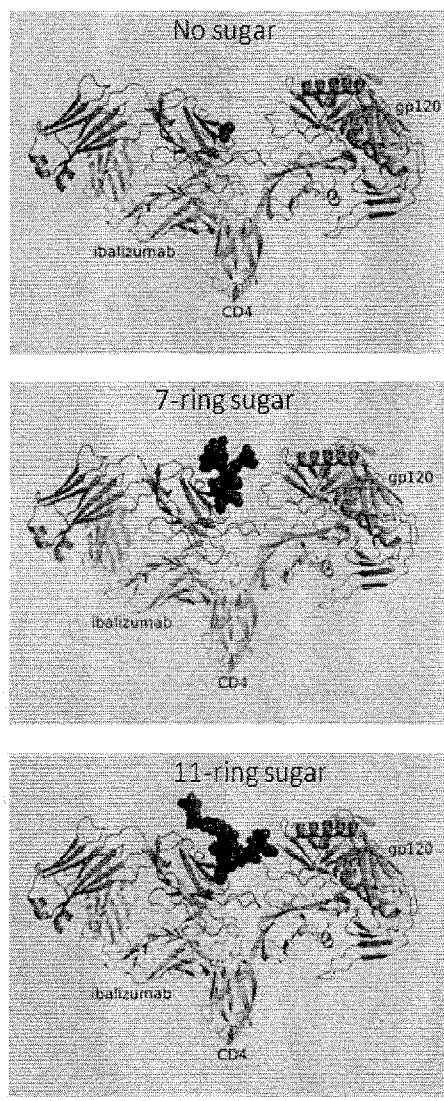

Whether glycan size influences the improved HIV-1 neutralization activity of the LMs was studied. The study was focused on LM52 because of its superior HIV-1 neutralization profile (FIG. 7). To produce a version of LM52 lacking any N-linked glycan, tunicamycin was added, which inhibited GlcNAc phosphotransferase, to 293A cells immediately after transient transfection with the LM52 construct. Similarly, to produce a version of LM52 tagged with glycans of 10-11 rings (the high Man-type N-glycan $Man_8GlcNAc_2$ (Man8) or $Man_9GlcNAc_2$ (Man9)) we added kifunensine to 293A cells. Lastly, to produce a version of LM52 bearing a 7-ring glycan (high mannose (Man)-type N-glycan $Man_5GlcNAc_2$ (Man5)), N-acetylglucosaminyltransferase 1-negative GnT1(−) HEK293S cells were used. As shown by SDS-PAGE, although the addition of kifunensine did not noticeably change the size of the L chain, addition of tunicamycin or growth in GnT1(−) cells noticeably reduced the size of the L chain (FIG. 8A). Similarly, the neutralization activities against three HIV-1 strains were more severely reduced for antibodies produced in the presence of tunicamycin or in GnT1(−) cells than for the antibody produced in the presence of kifunensine (FIG. 8B). Thus, stronger HIV-1-neutralizing activity was observed when larger glycans were present in the L chain at residue 52. Modeling suggests that larger glycans better fill the space between the L chain and gp120 (FIG. 4C), but the nature of the branching of the glycan may also affect the HIV-1 neutralizing activity of LM52.

Example 5

Neutralization Breadth and Potency of LM52

Figure 5:
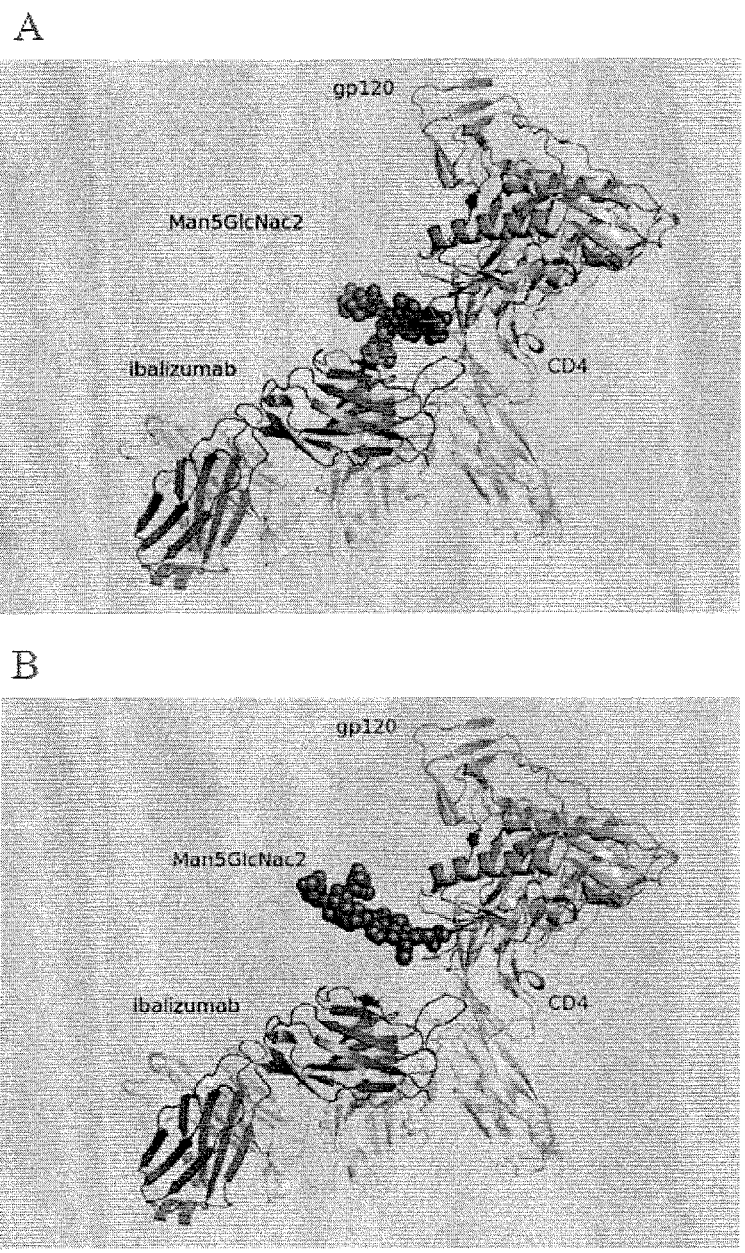
Figure 9:
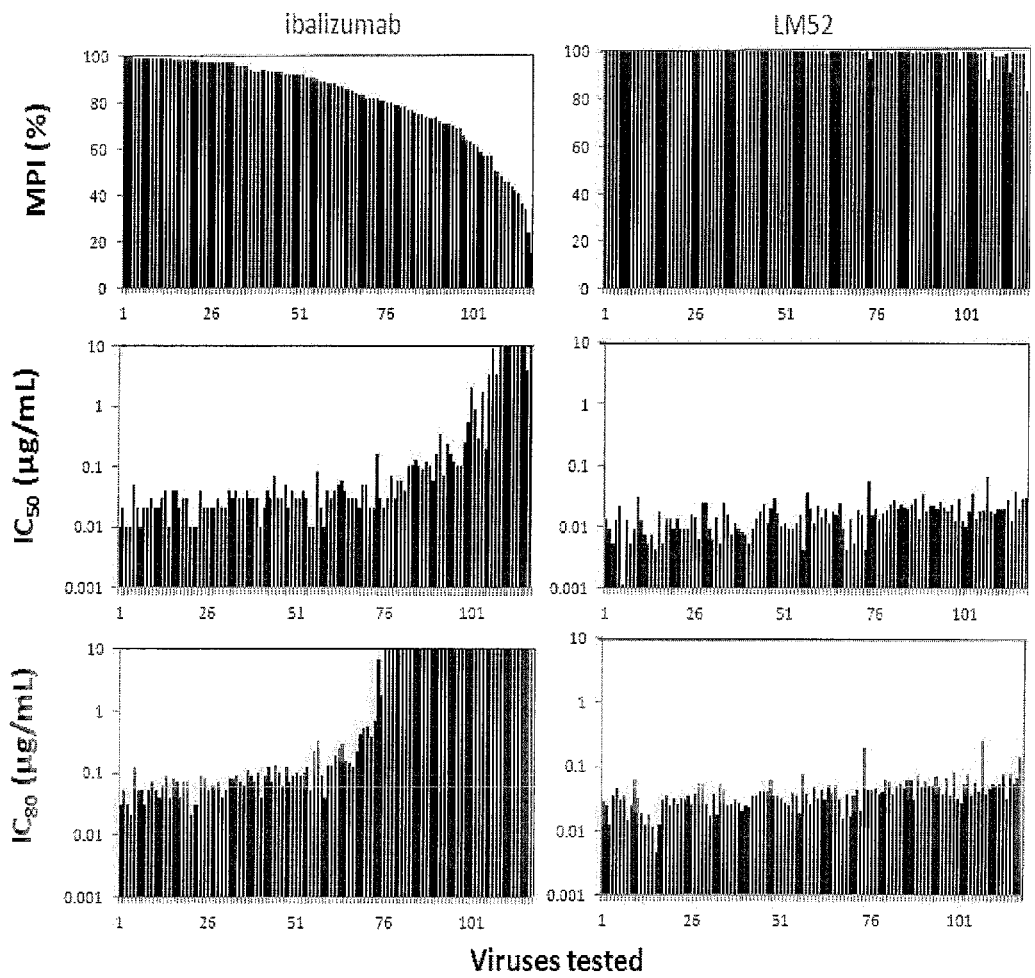
FIG. 9 shows the neutralization of a panel of 118 HIV-1 Env pseudoviruses; wherein the neutralization by LM52 and WT ibalizumab was measured in a TZM-b1 assay; wherein for each virus, black bars indicated maximum percent inhibition (MPI) when tested at Ab concentrations up to 10 μg/mL, and the corresponding $IC_{50}$ (μg/mL) or $IC_{80}$ (μg/mL); viruses were ordered by descending MPI for ibalizumab; given the large of number of viruses being tested, this experiment was done only once.

We then tested the HIV-1 neutralization activity of LM52 against a panel of 118 diverse HIV-1 viral strains covering 11 clades. LM52 showed significantly improved neutralization breadth and potency compared to WT ibalizumab in this single-cycle TZM-b1 assay (FIG. 9 and Table 3). LM52 had no neutralizing activity against the negative control virus (murine leukemia virus) (Table 3), but it neutralized (as defined by ≥50% inhibition) all HIV-1 strains tested, compared to 92% of strains for WT ibalizumab. In fact, LM52 neutralized 97% of viruses to ≥95% inhibition, compared to only 31% for WT ibalizumab (FIG. 5, upper panels). LM52 also exhibited $IC_{50}$ values of <0.1 μg/mL for all 118 viruses, compared to 75% of viruses for WT ibalizumab (FIG. 9, middle panels). Indeed, all of the viruses were neutralized by LM52 with an $IC_{80}$<0.3 μg/mL, whereas 36% of the viruses were not neutralized by 80% with WT ibalizumab even at a concentration of 10 μg/mL (FIG. 9, lower panels).

TABLE 3

In vitro neutralization profiles of ibalizumab and LM52 as expressed by $IC_{50}$ (μg/mL), $IC_{80}$ (μg/mL) and MPI (%)

| | | Ibalizumab | | | LM52 | | |
|---|---|---|---|---|---|---|---|
| Virus | Clade | $IC_{50}$ (μg/ml) | $IC_{80}$ (μg/ml) | MPI (%) | $IC_{50}$ (μg/ml) | $IC_{80}$ (μg/ml) | MPI (%) |
| 6535.3 | B | 0.01 | 0.05 | 99 | 0.012 | 0.034 | 100 |
| QH0692.42 | B | 0.03 | 0.14 | 85 | 0.023 | 0.051 | 100 |
| SC422661.8 | B | 0.04 | >10 | 77 | 0.019 | 0.037 | 100 |
| PVO.4 | B | 0.02 | 0.09 | 89 | 0.019 | 0.036 | 100 |
| TRO.11 | B | 0.01 | 0.05 | 91 | 0.015 | 0.035 | 100 |
| AC10.0.29 | B | 0.02 | 0.04 | 98 | 0.013 | 0.029 | 100 |
| RHPA4259.7 | B | >10 | >10 | 42 | 0.027 | 0.076 | 91 |
| THRO4156.18 | B | 0.06 | >10 | 78 | 0.022 | 0.062 | 99 |
| REJO4541.67 | B | 0.02 | 0.37 | 82 | 0.015 | 0.043 | 99 |
| TRJO4551.58 | B | 2.05 | >10 | 62 | 0.01 | 0.027 | 100 |
| WITO4160.33 | B | 0.02 | 0.43 | 83 | 0.013 | 0.036 | 100 |
| CAAN5342.A2 | B | 0.01 | 0.03 | 100 | 0.013 | 0.028 | 100 |
| WEAU_d15_410_5017 | B (T/F) | 0.02 | 10.00 | 80 | 0.019 | 0.043 | 100 |
| 1006_11_C3_1601 | B (T/F) | >10 | >10 | 46 | 0.019 | 0.053 | 98 |
| 1054_07_TC4_1499 | B (T/F) | 0.03 | >10 | 79 | 0.018 | 0.041 | 100 |
| 1056_10_TA11_1826 | B (T/F) | 0.01 | 0.02 | 98 | 0.013 | 0.031 | 100 |
| 1012_11_TC21_3257 | B (T/F) | 0.03 | 0.09 | 92 | 0.009 | 0.027 | 100 |
| 6240_08_TA5_4622 | B (T/F) | 0.02 | 0.05 | 99 | 0.0011 | 0.03 | 100 |
| 6244_13_B5_4576 | B (T/F) | 0.01 | 0.03 | 98 | 0.009 | 0.026 | 100 |
| 62357_14_D3_4589 | B (T/F) | 0.03 | 0.03 | 80 | 0.013 | 0.046 | 100 |
| SC05_8C11_2344 | B (T/F) | 0.01 | 9.49 | 97 | 0.009 | 0.032 | 100 |
| Du156.12 | C | 0.01 | 0.03 | 100 | 0.005 | 0.012 | 100 |
| Du172.17 | C | 0.01 | 0.04 | 88 | 0.011 | 0.026 | 100 |
| Du422.1 | C | 0.03 | 0.07 | 98 | 0.013 | 0.035 | 100 |
| ZM197M.PB7 | C | 0.01 | 0.02 | 99 | 0.012 | 0.034 | 100 |
| ZM214M.PL15 | C | 0.01 | 0.04 | 94 | 0.005 | 0.024 | 100 |
| ZM233M.PB6 | C | 0.03 | 1.84 | 81 | 0.015 | 0.043 | 100 |
| ZM249M.PL1 | C | 0.03 | 0.12 | 91 | 0.011 | 0.038 | 100 |
| ZM53M.PB12 | C | 0.10 | >10 | 77 | 0.022 | 0.051 | 100 |
| ZM109F.PB4 | C | 3.90 | >10 | 24 | 0.028 | 0.064 | 99 |
| ZM135M.P10a | C | 0.10 | >10 | 66 | 0.012 | 0.035 | 100 |
| CAP45.2.00.G3 | C | 0.03 | 0.09 | 93 | 0.009 | 0.029 | 100 |
| CAP210.2.00.E8 | C | 0.05 | 0.12 | 99 | 0.021 | 0.046 | 100 |
| HIV-001428-2.42 | C | >10 | >10 | 36 | 0.036 | 0.077 | 99 |
| HIV-0013095-2.11 | C | 0.29 | >10 | 59 | 0.035 | 0.075 | 100 |
| HIV-16055-2.3 | C | 0.11 | >10 | 76 | 0.02 | 0.053 | 100 |
| HIV-16845-2.22 | C | 0.06 | 0.29 | 86 | 0.017 | 0.049 | 100 |

TABLE 3-continued

In vitro neutralization profiles of ibalizumab and LM52 as expressed by
IC$_{50}$ (µg/mL), IC$_{80}$ (µg/mL) and MPI (%)

| Virus | Clade | Ibalizumab | | | LM52 | | |
|---|---|---|---|---|---|---|---|
| | | IC$_{50}$ (µg/ml) | IC$_{80}$ (µg/ml) | MPI (%) | IC$_{50}$ (µg/ml) | IC$_{80}$ (µg/ml) | MPI (%) |
| Ce1086_B2 | C (T/F) | 0.04 | 0.09 | 97 | 0.009 | 0.031 | 100 |
| Ce0393_C3 | C (T/F) | 0.02 | 0.03 | 99 | 0.005 | 0.014 | 100 |
| Ce1176_A3 | C (T/F) | 0.04 | 0.11 | 94 | 0.011 | 0.025 | 100 |
| Ce2010_F5 | C (T/F) | 0.05 | 0.24 | 87 | 0.011 | 0.029 | 100 |
| Ce0682_E4 | C (T/F) | 0.05 | 0.52 | 82 | 0.005 | 0.017 | 100 |
| Ce1172_H1 | C (T/F) | 0.03 | 0.07 | 93 | 0.008 | 0.027 | 100 |
| Ce2060_G9 | C (T/F) | >10 | >10 | 41 | 0.012 | 0.031 | 100 |
| Ce703010054_2A2 | C (T/F) | 9.01 | >10 | 51 | 0.062 | 0.255 | 88 |
| BF1266.431a | C (T/F) | 0.02 | 0.05 | 99 | 0.009 | 0.024 | 100 |
| 246F C1G | C (T/F) | 0.34 | >10 | 71 | 0.021 | 0.049 | 100 |
| 249M B10 | C (T/F) | 0.03 | 0.10 | 94 | 0.007 | 0.02 | 100 |
| ZM247v1(Rev-) | C (T/F) | 0.09 | >10 | 74 | 0.028 | 0.061 | 100 |
| 7030102001E5(Rev-) | C (T/F) | 0.02 | 0.02 | 97 | 0.015 | 0.034 | 100 |
| 1394C9G1(Rev-) | C (T/F) | 0.02 | 0.05 | 97 | 0.014 | 0.026 | 100 |
| Ce704809221_1B3 | C (T/F) | 0.16 | >10 | 70 | 0.02 | 0.048 | 99 |
| CNE19 | BC | 0.06 | >10 | 78 | 0.027 | 0.059 | 100 |
| CNE20 | BC | 0.03 | 0.06 | 92 | 0.019 | 0.041 | 100 |
| CNE21 | BC | 0.08 | 0.32 | 89 | 0.035 | 0.074 | 100 |
| CNE17 | BC | 0.04 | 0.15 | 86 | 0.015 | 0.038 | 100 |
| CNE30 | BC | 0.10 | >10 | 73 | 0.033 | 0.071 | 99 |
| CNE52 | BC | 0.12 | >10 | 69 | 0.017 | 0.037 | 100 |
| CNE53 | BC | 3.36 | >10 | 57 | 0.018 | 0.04 | 100 |
| CNE58 | BC | 0.03 | 0.07 | 93 | 0.017 | 0.035 | 100 |
| MS208.A1 | A | 0.03 | 0.07 | 99 | 0.029 | 0.063 | 100 |
| Q23.17 | A | 3.40 | >10 | 50 | 0.017 | 0.037 | 100 |
| Q461.e2 | A | 0.05 | 0.54 | 82 | 0.018 | 0.035 | 100 |
| Q769.d22 | A | >10 | >10 | 34 | 0.019 | 0.052 | 99 |
| Q259.d2.17 | A | 0.04 | 0.19 | 87 | 0.019 | 0.043 | 99 |
| Q842.d12 | A | 0.02 | 0.09 | 93 | 0.009 | 0.023 | 100 |
| 0330.v4.c3 | A | 0.25 | >10 | 64 | 0.028 | 0.078 | 97 |
| 0260.v5.c36 | A | 0.04 | 0.12 | 93 | 0.013 | 0.035 | 100 |
| 191955_A11 | A (T/F) | 0.04 | 0.09 | 96 | 0.023 | 0.052 | 100 |
| 191084 B7-19 | A (T/F) | 0.04 | 0.10 | 91 | 0.009 | 0.024 | 100 |
| 9004SS_A3_4 | A (T/F) | 0.04 | 0.13 | 88 | 0.021 | 0.048 | 100 |
| T257-31 | CRF02_AG | 0.02 | 0.05 | 99 | 0.012 | 0.032 | 100 |
| 928-28 | CRF02_AG | 0.05 | 0.12 | 92 | 0.028 | 0.063 | 100 |
| 263-8 | CRF02_AG | 0.02 | 0.07 | 92 | 0.016 | 0.035 | 100 |
| T250-4 | CRF02_AG | 0.02 | 0.06 | 97 | 0.023 | 0.052 | 100 |
| T251-18 | CRF02_AG | 0.03 | 0.07 | 97 | 0.023 | 0.052 | 100 |
| T278-50 | CRF02_AG | >10 | >10 | 48 | 0.016 | 0.045 | 98 |
| T255-34 | CRF02_AG | 0.90 | >10 | 61 | 0.017 | 0.052 | 100 |
| 211-9 | CRF02_AG | 0.03 | 0.07 | 96 | 0.015 | 0.043 | 100 |
| 235-47 | CRF02_AG | 0.02 | 0.04 | 97 | 0.009 | 0.026 | 100 |
| 620345.c01 | CRF01_AE | 0.03 | 0.22 | 83 | 0.004 | 0.015 | 100 |
| 703357.c02 | CRF01_AE | 0.02 | 0.05 | 100 | 0.009 | 0.024 | 100 |
| C1080.c03 | CRF01_AE | 0.03 | 0.12 | 84 | 0.009 | 0.029 | 100 |
| R2184.c04 | CRF01_AE | 0.03 | 0.06 | 96 | 0.007 | 0.024 | 100 |
| R1166.c01 | CRF01_AE | 0.02 | 0.05 | 97 | 0.006 | 0.017 | 100 |
| R3265.c06 | CRF01_AE | 0.02 | 0.67 | 82 | 0.004 | 0.02 | 100 |
| C2101.c01 | CRF01_AE | 0.04 | 0.08 | 97 | 0.014 | 0.037 | 100 |
| C3347.c11 | CRF01_AE | 0.01 | 0.04 | 98 | 0.004 | 0.011 | 100 |
| C4118.c09 | CRF01_AE | 0.04 | 0.09 | 92 | 0.01 | 0.034 | 100 |
| CNE5 | CRF01_AE | 0.04 | 0.08 | 98 | 0.017 | 0.045 | 100 |
| BJOX009000.02.4 | CRF01_AE (T/F) | 0.03 | 0.10 | 92 | 0.011 | 0.031 | 100 |
| BJOX015000.11.5 | CRF01_AE (T/F) | 0.03 | 0.13 | 88 | 0.006 | 0.036 | 100 |
| BJOX00000.06.2 | CRF01_AE (T/F) | 0.02 | 0.04 | 99 | 0.007 | 0.019 | 100 |
| BJOX025000.01.1 | CRF01_AE (T/F) | 0.02 | 0.06 | 97 | 0.014 | 0.031 | 100 |
| BJOX028000.10.3 | CRF01_AE (T/F) | 0.01 | 0.22 | 90 | 0.004 | 0.019 | 100 |
| X1193_c1 | G | 0.03 | 0.06 | 99 | 0.005 | 0.012 | 100 |
| PO402_c2_11 | G | 0.04 | 0.09 | 99 | 0.007 | 0.018 | 100 |
| X1254_c3 | G | 0.13 | >10 | 75 | 0.019 | 0.044 | 100 |
| X2088_c9 | G | 0.07 | >10 | 79 | 0.016 | 0.036 | 100 |
| X2131_C1_B5 | G | 0.20 | >10 | 57 | 0.017 | 0.056 | 99 |
| P91981_C5_3 | G | 0.12 | >10 | 73 | 0.013 | 0.029 | 100 |
| X1632_S2_B10 | G | >10 | >10 | 15 | 0.03 | 0.143 | 83 |
| 3016.v5.c45 | D | 0.07 | 0.13 | 93 | 0.022 | 0.041 | 100 |
| A07412M1.vrc12 | D | 1.76 | >10 | 57 | 0.013 | 0.035 | 99 |

TABLE 3-continued

In vitro neutralization profiles of ibalizumab and LM52 as expressed by
$IC_{50}$ (µg/mL), $IC_{80}$ (µg/mL) and MPI (%)

| | | Ibalizumab | | | LM52 | | |
|---|---|---|---|---|---|---|---|
| Virus | Clade | $IC_{50}$ (µg/ml) | $IC_{80}$ (µg/ml) | MPI (%) | $IC_{50}$ (µg/ml) | $IC_{80}$ (µg/ml) | MPI (%) |
| 231965.c01 | D | 0.10 | >10 | 69 | 0.022 | 0.066 | 100 |
| 231966.c02 | D | 0.03 | 0.08 | 96 | 0.005 | 0.018 | 100 |
| 191821_E6_1 | D (T/F) | 0.10 | >10 | 75 | 0.022 | 0.06 | 99 |
| 3817.v2.c59 | CD | 0.04 | 0.07 | 98 | 0.005 | 0.012 | 100 |
| 6480.v4.c25 | CD | 0.03 | 0.10 | 93 | 0.011 | 0.04 | 100 |
| 6952.v1.c20 | CD | 0.07 | >10 | 71 | 0.019 | 0.051 | 100 |
| 6811.v7.c18 | CD | 0.16 | >10 | 72 | 0.021 | 0.058 | 100 |
| 89-F1_2_25 | CD | 0.16 | 6.54 | 81 | 0.053 | 0.195 | 97 |
| 3301.v1.c24 | AC | 0.55 | >10 | 63 | 0.012 | 0.032 | 100 |
| 6041.v3.c23 | AC | >10 | >10 | 46 | 0.019 | 0.051 | 98 |
| 6540.v4.c1 | AC | 0.06 | >10 | 74 | 0.017 | 0.047 | 100 |
| 6545.v4.c1 | AC | 0.23 | >10 | 71 | 0.025 | 0.069 | 99 |
| 0815.v3.c3 | ACD | >10 | >10 | 44 | 0.019 | 0.053 | 99 |
| 13103.v3.c10 | ACD | 0.03 | 0.07 | 98 | 0.009 | 0.024 | 100 |
| Murine leukemia virus | Control | ND | ND | ND | >10 | >10 | 3 |

Figure 11:
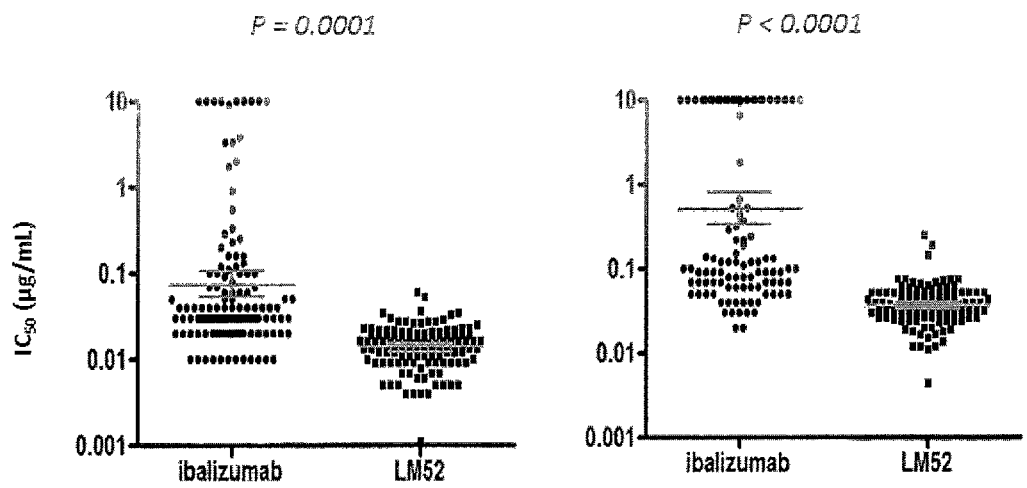
FIG. 11 provides the summary of the neutralization activity of LM52 and ibalizumab against a diverse panel of 118 HIV-1 Env pseudoviruses, as reflected by their $IC_{50}$ (μg/mL) and $IC_{80}$ (μg/mL); wherein red lines showed the geometric mean values and the 95% confidence interval (each dot represents an individual viral strain).
Figure 12:
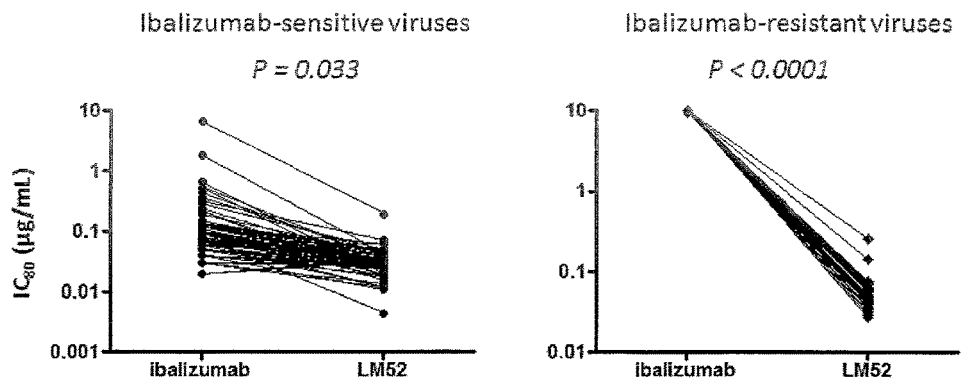
FIG. 12 shows the $IC_{80}$ values of LM52 and ibalizumab against ibalizumab-sensitive or ibalizumab-resistant viruses (resistance defined as $IC_{80}>10$ μg/mL).
Figure 13:
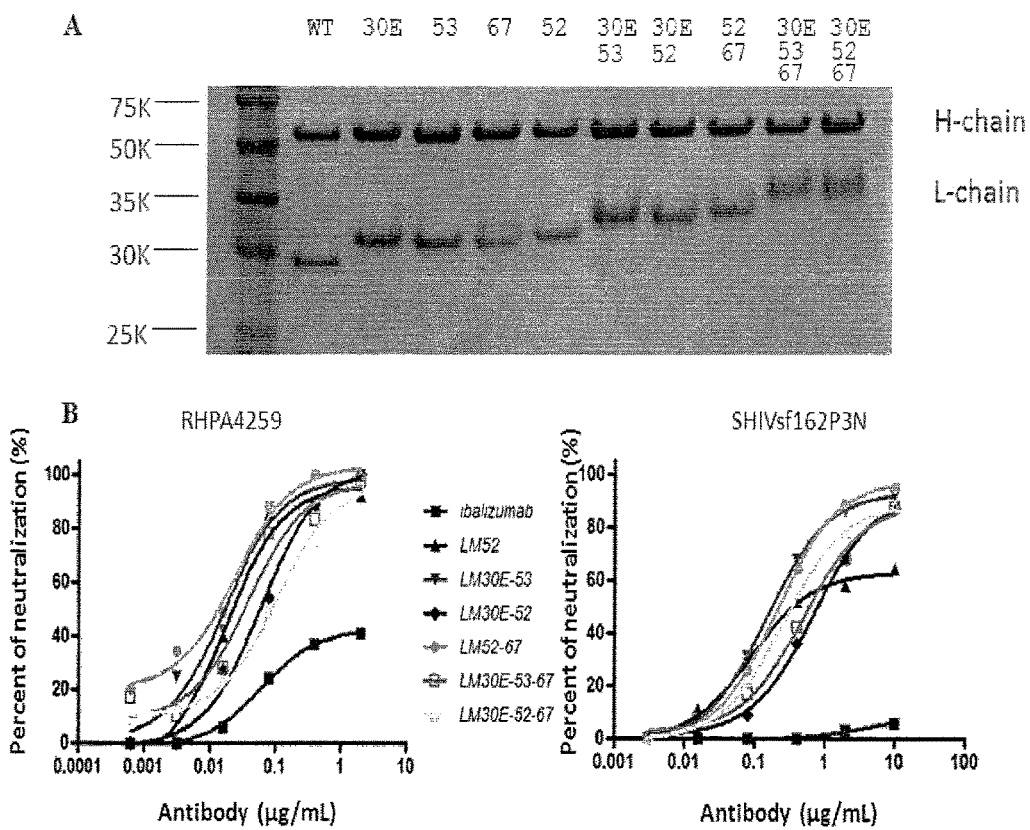
FIG. 13A shows the sizes of H chain and L chain of ibalizumab and its single, double and triple glycan variants as analyzed by SDS-PAGE.
FIG. 13B shows the neutralization activities of ibalizumab, LM52, and several double or triple glycan mutants against two ibalizumab-resistant pseudoviruses in TZM-b1 cells.

Overall, the geometric mean $IC_{50}$ value for LM52 was 14 ng/mL, compared to 74 ng/mL for WT ibalizumab, and the geometric mean $IC_{80}$ value for LM52 was 37 ng/mL, compared to 510 ng/mL for WT ibalizumab (FIG. 11). When the viruses were separated into ibalizumab-sensitive (MPI≥80%) and ibalizumab-resistant strains (MPI≤80%), it was evident that the enhanced potency of LM52 was most obvious in ibalizumab-resistant viruses (FIG. 12). In ibalizumab-resistant viruses, the geometric mean $IC_{80}$ value for LM52 was 50 ng/mL, compared to almost 10,000 ng/mL for WT ibalizumab. The potency of LM52 was enhanced by about 3-fold even in ibalizumab-sensitive viruses.

Figure 10:
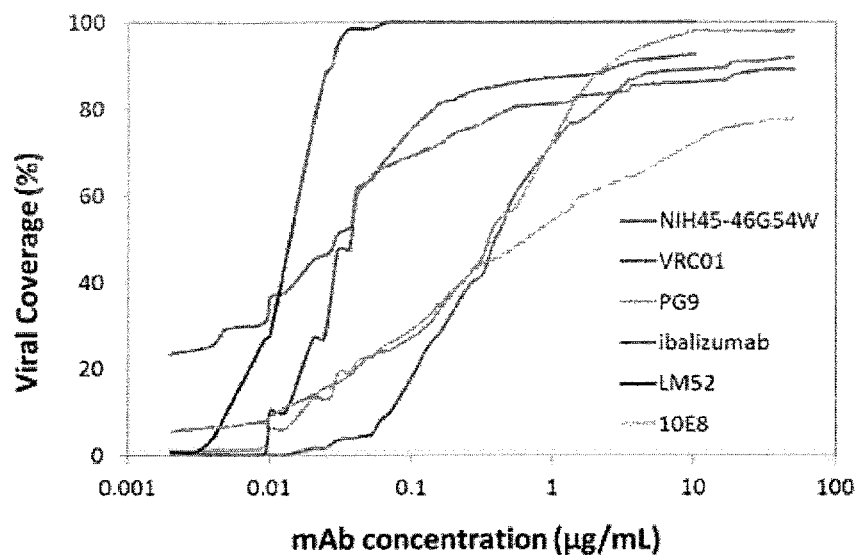
FIG. 10 shows that HIV-1 strain coverage of LM52. Viral coverage of WT ibalizumab, LM52, and PG9, 10E8, VRC01, and NIH45-46G54W HIV-1 bnAb. LM52 and ibalizumab were tested up to 10 μg/mL, while the other monoclonal antibodies were tested up to 50 μg/mL.

The improved activity of LM52 was also evident in a plot comparing its HIV-1 strain coverage across increasing antibody concentrations (FIG. 10). The improvement over WT ibalizumab was readily apparent, as was its superiority over mAbs (PG9, VRC01, 10E8, and NIH45-46G54W) known for their broad and potent HIV-1 neutralizing activity. LM52 had the greatest viral coverage at all concentrations >0.01 µg/mL and it reached 100% at a concentration less than 0.1 µg/mL. Only at concentrations below 0.01 µg/mL was LM52 coverage inferior to NIH45-46G54W, a modified version of a human mAb directed to the CD4-binding site on gp120. It should be noted, however, that ibalizumab inhibits HIV-1 infection by binding to CD4, while VRC01, PG9, 10E8, and NIH45-46 G54W inhibit HIV-1 infection by binding directly to the virus. Nonetheless, regardless of whether these mAbs bind viral envelope or CD4, they all neutralize HIV-1 infection by blocking viral entry.

Example 6

Effects of Multiple Glycans

We next examined the effect of placing two or three glycans in the region of interest in the ibalizumab L chain. We produced LM30E-52, LM30E-53, and LM52-67 double mutants, as well as LM30E-52-67 and LM30E-53-67 triple mutants in 293A cells and then purified and analyzed the antibodies by SDS-PAGE (FIG. 13A). Compared to wild-type (WT) ibalizumab or single mutant LMs, slightly bigger L chain was observed in each of the double mutants, and an even bigger L chain was observed in each of the triple mutants. We next explored the HIV-1 neutralization profile of these variant mAbs against a panel of HIV-1 strains known to be fully or partially resistant to ibalizumab. In general, the double and triple mutants showed neutralizing activity comparable to that of LM52 (Table 4; FIG. 13B, left panel). In fact, the geometric mean $IC_{80}$ values suggest that the triple mutants may be slightly less potent compared to LM52. The only exception noted was for SHIVsf162P3N, a virus more sensitive to the double and triple mutants than to LM52 (Table 4; FIG. 13B, right panel). Overall, we found no evidence that adding more than one glycan further improves the HIV-1 neutralization profile of LM52 against ibalizumab-sensitive viruses. The improvement to LM52 by the addition of a second glycan may only be apparent with viruses resistant or partially resistant to LM52.

TABLE 4

Comparison of the $IC_{80}$ (μg/mL) of ibalizumab and its single, double, and triple LMs

| Virus | ibalizumab | LM52 | LM30E-53 | LM30E-52 | LM52-67 | LM30E-53-67 | LM30E-52-67 |
|---|---|---|---|---|---|---|---|
| RHPA4259 | >10 | 0.03 | 0.02 | 0.10 | 0.02 | 0.06 | 0.23 |
| SHIVsf162P3 | >10 | 0.37 | 0.32 | 0.61 | 0.37 | 0.68 | 0.89 |
| SHIVsf162P3N | >10 | >10 | 0.93 | 4.40 | 0.98 | 4.40 | 2.50 |
| 9015-07 A1 | 0.24 | 0.04 | 0.04 | 0.06 | 0.04 | 0.08 | 0.13 |
| 1051-D927 TD12 | >10 | 0.05 | 0.09 | 0.09 | 0.04 | 0.32 | 0.32 |
| Q769.d22 | >10 | 0.13 | 0.15 | 0.29 | 0.11 | 0.47 | 0.49 |
| 16055-2.3 | >10 | 0.04 | 0.06 | 0.08 | 0.05 | 0.13 | 0.24 |
| 246F C1G C | >10 | 0.07 | 0.10 | 0.22 | 0.02 | 0.30 | 0.49 |
| QG393.60M | >10 | 0.05 | 0.05 | 0.07 | 0.04 | 0.10 | 0.11 |
| ZM249M.PL1 | 0.22 | 0.05 | 0.06 | 0.12 | 0.05 | 0.10 | 0.13 |
| Q259.d2.17 | 0.37 | 0.09 | 0.10 | 0.15 | 0.07 | 0.13 | 0.26 |

TABLE 4-continued

Comparison of the $IC_{80}$ (μg/mL) of ibalizumab and its single, double, and triple LMs

| Virus | ibalizumab | LM52 | LM30E-53 | LM30E-52 | LM52-67 | LM30E-53-67 | LM30E-52-67 |
|---|---|---|---|---|---|---|---|
| Q461.e2 | 0.61 | 0.09 | 0.10 | 0.14 | 0.09 | 0.16 | 0.18 |
| Geometric Mean | 3.20 | 0.10 | 0.09 | 0.18 | 0.07 | 0.22 | 0.31 |

Example 7

Analysis of LM52 Polyreactivity

Figure 14:
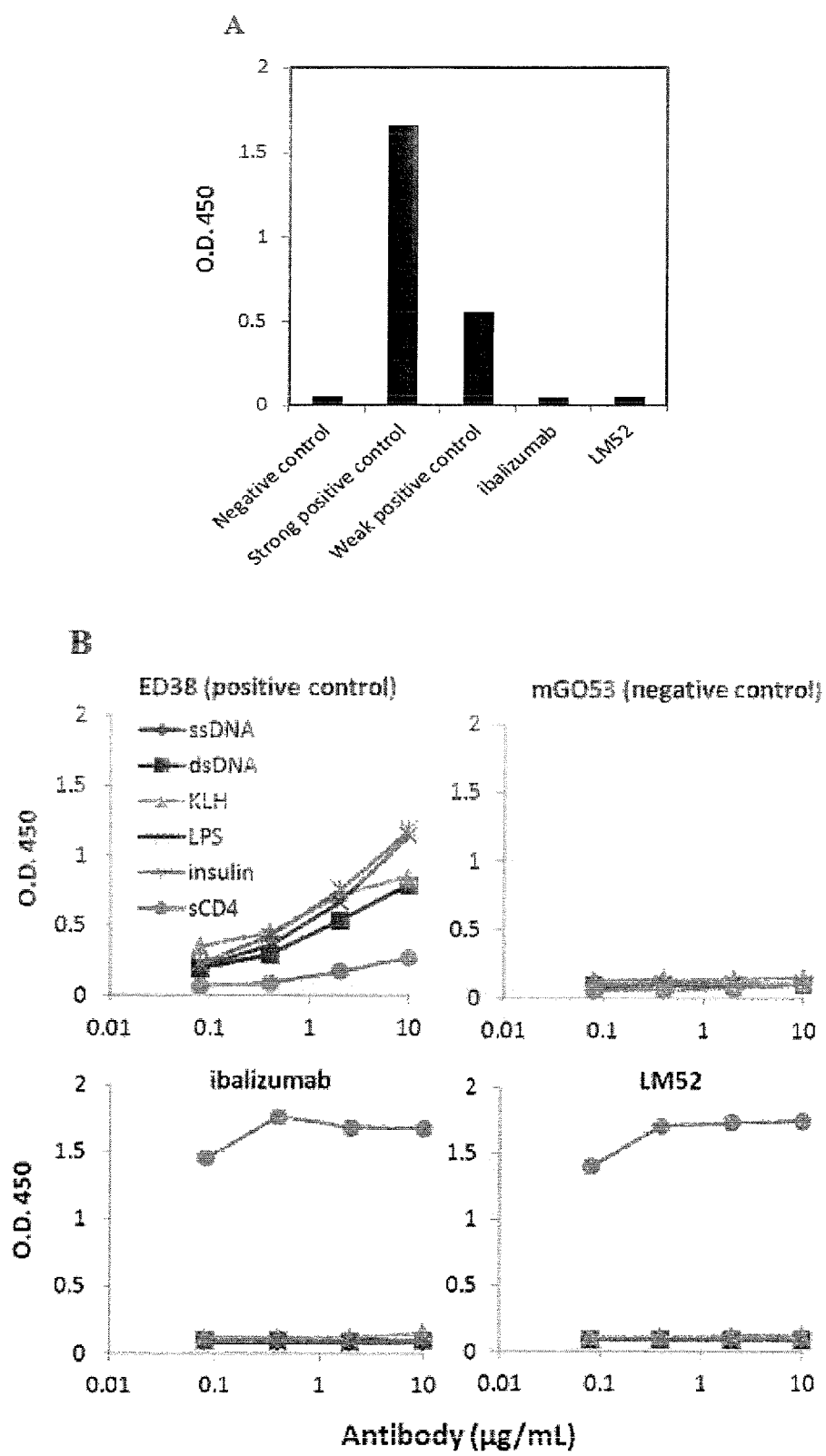
FIGS. 14A and 14B provide the results of the analysis of LM52 polyreactivity; where

A property common to some HIV-1-neutralizing mAbs is their cross-reactivity with self-antigens[29, 30]. Neither LM52 nor ibalizumab bound to HEp-2 epithelial cell extracts (FIG. 14A) even at concentrations of 10 μg/mL. In addition, neither LM52 nor ibalizumab showed reactivity with single-stranded DNA, double-stranded DNA, insulin, lipopolysaccharide, or keyhole limpet hemocyanin (KLH) (FIG. 14B). Human CD4 protein, the intended target of ibalizumab, was the only self antigen tested that was recognized by LM52. Thus, we find no evidence that LM52 is polyreactive with self-antigens.

CONCLUSION

In the present invention, a superior HIV-1 entry-blocking mAb product generated from the MV1, called as the variant LM52, is provided, which at relatively low concentrations could neutralize all tested HIV-1 strains tested. The virus-neutralizing properties of LM52 were evidently superior to those of the wild type of ibalizumab as well as of a number of the best anti-Env mAbs reported to date, for example VRC01, PG9, 10E8, and NIH45-46G54W. Together with the established safety record of the ibalizumab in humans, these observations suggest that LM52 should be a good candidate for clinical development for the treatment or prevention of HIV-1. This modified antibody may be particularly suitable as a long-acting PrEP agent given its expected (based on the known pharmacokinetic properties of the parental ibalizumab) schedule of monthly administration.

These findings also provide insight into the mechanism of action of ibalizumab. That HIV-1 loses a glycan in the N-terminus of gp120 V5 to become resistant to ibalizumab. It is suggested that the ibalizumab mechanism of action is mediated by the glycan resulting in a steric clash between the antibody L chain and the viral envelope glycoprotein, thereby sterically disrupting a step in HIV-1 entry. It is indicated in this invention that a glycan on the L chain restores the antiviral activity of ibalizumab against ibalizumab-resistant strains, that positioning this glycan on key residues spatially closest to V5 resulted in greatest antiviral effect, and that larger glycans conferred larger effects on virus neutralization collectively support that ibalizumab blocks HIV-1 infection via a steric hindrance mechanism.

All publications and patents, patent application publications, and patent applications cited herein are hereby incorporated by reference to the same extent as if they had each been individually incorporated by reference.

What is claimed is:

1. A glycan-modified antibody comprising N-linked glycans attached to a variable region of said antibody, wherein said antibody comprises a heavy chain comprising three CDRs contained in SEQ ID NO: 2 and a light chain comprising three CDRs contained in SEQ ID NO:3, and comprises an engineered N-linked glycosylation site at an amino acid position in the sequence of SEQ ID NO:3 selected from the group consisting of amino acid 54 of SEQ ID NO:3 (30EGln), amino acid 77 of SEQ ID NO:3 (52Ser), amino acid 78 of SEQ ID NO:3 (53Thr), amino acid 79 of SEQ ID NO:3 (54Arg), amino acid 85 of SEQ ID NO:3 (60Asp), amino acid 90 of SEQ ID NO:3 (65Ser), amino acid 92 of SEQ ID NO:3 (67Ser), and amino acid 101 of SEQ ID NO:3 (76Ser).

2. The antibody of claim 1, wherein the one or more N-linked glycans are attached to the variable region of the light chain of said antibody.

3. The antibody of claim 1, wherein the engineered N-linked glycosylation site is located at an amino acid position of the light chain selected from the group consisting of 30EGln, 52Ser, 53Thr, 54Arg, 65Ser, and 67Ser.

4. The antibody of claim 3, wherein the engineered N-linked glycosylation site is located at 52Ser.

5. The antibody of claim 4, wherein said light chain comprises an amino acid sequence of the light chain as set forth in SEQ ID NO: 4.

6. A glycan-modified antibody comprising N-linked glycans attached to a variable region of said antibody, wherein said antibody comprises a light chain and a heavy chain, wherein said light chain comprises an amino acid sequence of the light chain set forth in SEQ ID NO:4 and wherein said heavy chain comprises an amino acid sequence of the heavy chain as set forth in SEQ ID NO: 5.

7. The antibody of claim 1, wherein the N-linked glycans comprise at least 7 carbohydrate units.

8. The antibody of claim 7, wherein the N-linked glycans comprise 10-11 carbohydrate units.

9. A pharmaceutical composition comprising the antibody of claim 1 and at least one pharmaceutically acceptable carrier.

10. A pharmaceutical composition comprising the antibody of claim 6 and at least one pharmaceutically acceptable carrier.

* * * * *

UNITED STATES PATENT AND TRADEMARK OFFICE
CERTIFICATE OF CORRECTION

PATENT NO.        : 9,790,276 B2              Page 1 of 1
APPLICATION NO.   : 14/132667
DATED             : October 17, 2017
INVENTOR(S)       : Song et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 73 days.

Signed and Sealed this

Twenty-fifth Day of September, 2018

Andrei Iancu
*Director of the United States Patent and Trademark Office*